United States Patent
Burghardt et al.

(10) Patent No.: US 11,680,033 B2
(45) Date of Patent: *Jun. 20, 2023

(54) PROCESS FOR PREPARING METHACROLEIN FROM FORMALDEHYDE AND PROPIONALDEHYDE AND PREPARATION PLANT FOR THE PURPOSE

(71) Applicant: Röhm GmbH, Darmstadt (DE)

(72) Inventors: Rudolf Burghardt, Darmstadt (DE); Steffen Krill, Muehltal (DE); Florian Zschunke, Frankfurt (DE); Eduard Rundal, Frankfurt (DE); Torsten Panak, Stockstadt/Rhein (DE); Daniel Helmut König, Stuttgart (DE)

(73) Assignee: Röhm GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/753,240

(22) PCT Filed: Aug. 20, 2020

(86) PCT No.: PCT/EP2020/073343
§ 371 (c)(1),
(2) Date: Feb. 24, 2022

(87) PCT Pub. No.: WO2021/037669
PCT Pub. Date: Mar. 4, 2021

(65) Prior Publication Data
US 2022/0298094 A1 Sep. 22, 2022

(30) Foreign Application Priority Data
Aug. 30, 2019 (EP) .................................... 19194674

(51) Int. Cl.
| C07C 45/75 | (2006.01) |
| C07C 45/84 | (2006.01) |
| B01D 3/14 | (2006.01) |
| B01D 5/00 | (2006.01) |
| B01D 17/02 | (2006.01) |
| B01J 14/00 | (2006.01) |

(52) U.S. Cl.
CPC .............. *C07C 45/75* (2013.01); *B01D 3/145* (2013.01); *B01D 5/006* (2013.01); *B01D 17/0214* (2013.01); *B01J 14/005* (2013.01); *C07C 45/84* (2013.01)

(58) Field of Classification Search
CPC ................................ C07C 45/75; C07C 45/82
USPC ......................................................... 568/461
See application file for complete search history.

(56) References Cited

U.S. PATENT DOCUMENTS

| 4,496,770 A | 1/1985 | Duembgen et al. |
| 9,580,374 B2 | 2/2017 | Krill et al. |
| 9,611,204 B2 | 4/2017 | Burghardt et al. |
| 9,816,703 B2 | 11/2017 | Krill et al. |
| 9,994,507 B2 | 6/2018 | Burghardt et al. |
| 10,125,077 B2 | 11/2018 | Krill et al. |
| 2016/0138804 A1 | 5/2016 | Krill et al. |
| 2016/0159719 A1 | 6/2016 | Burghardt et al. |
| 2016/0200660 A1 | 7/2016 | Krill et al. |
| 2017/0275227 A1 | 9/2017 | Burghardt et al. |
| 2017/0305830 A1 | 10/2017 | Krill et al. |
| 2021/0363089 A1 | 11/2021 | Lygin et al. |

FOREIGN PATENT DOCUMENTS

| DE | 3213681 | 10/1983 |
| JP | 2829531 | 1/2015 |
| WO | 2015/065610 | 5/2015 |
| WO | 2016/042000 | 3/2016 |
| WO | 2018/217961 | 11/2018 |
| WO | 2018/217963 | 11/2018 |
| WO | 2018/217964 | 11/2018 |

OTHER PUBLICATIONS

International Search Report dated Nov. 17, 2020 in PCT/EP2020/073343, with English translation, 5 pages.
Written Opinion dated Nov. 17, 2020 in PCT/EP2020/073343, with English translation, 9 pages.
U.S. Pat. No. 9,611,204, Apr. 4, 2017, 2016/0159719, Burghardt et al.
U.S. Appl. No. 17/269,648, filed Feb. 19, 2021, 2021/0363089, Lygin et al.
U.S. Pat. No. 9,816,703, Nov. 14, 2017, 2016/0138804, Krill et al.
U.S. Pat. No. 9,580,374, Feb. 28, 2017, 2016/0200660, Krill et al.
U.S. Pat. No. 9,994,507, Jun. 12, 2018, 2017/0275227, Burghardt et al.
U.S. Pat. No. 10,125,077, Nov. 13, 2018, 2017/0305830, Krill et al.
U.S. Office Action dated Aug. 17, 2022, in U.S. Appl. No. 17/753,232, 6 pages.
U.S. Appl. No. 17/753,232, filed Feb. 24, 2022, Burghardt et al.
Krill et al., U.S. Appl. No. 18/006,958, filed Jan. 26, 2023.
U.S. Appl. No. 18/006,958, filed Jan. 26, 2023, Krill et al.

*Primary Examiner* — Ana Z Muresan
(74) *Attorney, Agent, or Firm* — Grüneberg and Myers PLLC

(57) ABSTRACT

A process and a preparation plant prepares methacrolein from formaldehyde and propionaldehyde, in presence of water and a homogeneous catalyst based at least on an acid and a base. A reaction mixture is introduced into a methacrolein workup plant and separated in a first distillation column, into a first distillation mixture in a gas phase at the top and a second distillation mixture in a liquid phase at the bottom. The first distillation mixture is condensed and, in a first phase separator, the organic phase and the aqueous phase of the condensate are separated from one another. The aqueous phase is introduced into a second distillation column, that is not part of the methacrolein workup plant, and is separated into a third distillation mixture in a gas phase at the top and a fourth distillation mixture at the bottom. The third distillation mixture is introduced into the methacrolein workup plant.

17 Claims, 9 Drawing Sheets

PROCESS FOR PREPARING METHACROLEIN FROM FORMALDEHYDE AND PROPIONALDEHYDE AND PREPARATION PLANT FOR THE PURPOSE

CROSS-REFERENCE TO RELATED APPLICATIONS

This application is the National Stage entry under § 371 of International Application No. PCT/EP2020/073343, filed on Aug. 20, 2020, and which claims the benefit of priority to European Application No. 19194674.8, filed on Aug. 30, 2019. The content of each of these applications is hereby incorporated by reference in its entirety.

BACKGROUND OF THE INVENTION

Field of the Invention

The present invention relates to a process and to a preparation plant for preparing methacrolein from formaldehyde and propionaldehyde in the presence of water and in the presence of a homogeneous catalyst based at least on an acid and a base.

DESCRIPTION OF RELATED ART

Over and above a certain concentration of catalyst in the wastewater leaving the preparation plant, the wastewater is too problematic from an environmental point of view and can no longer be routed to a communal water treatment plant for disposal. The wastewater must either be treated in a complex manner or sent to an incineration in order to convert the problematic constituents to less problematic substances. Both are associated with technical complexity and energy expenditure. If catalyst is discharged from the preparation plant, it is lost from the preparation plant. It is then necessary to use new catalyst. This is associated with costs.

DE 3213681 A1 discloses a process in which methacrolein is prepared in a tubular reactor under elevated pressure in the liquid phase from formaldehyde and propionaldehyde in the presence of water and in the presence of a homogeneous catalyst. The reaction mixture is expanded to standard pressure and routed into a first distillation column. A gaseous stream containing methacrolein and water is drawn off from the top of the first distillation column. Water and catalyst collect in the bottom. The homogeneous catalyst is thus removed in the first distillation column. In addition, DE 3213681 A1 proposes a reactor operation that gives good reaction results with only a small amount of catalyst. In this way, less catalyst is required from the outset.

For the handling of the aqueous phase removed, which contains the homogeneous catalyst, i.e. the bottoms, DE 3213681 A1 proposes multiple variants. In a first variant, the bottoms are disposed of entirely. In a second variant, a portion of the bottoms is disposed of and the rest is returned to the reactor. In a third variant, the bottoms are sent to a second distillation column with which water is removed by distillation overhead. The concentration of the catalyst in the bottoms from the second distillation column is thus correspondingly higher than in the bottoms from the first distillation column. The bottoms from the second distillation column are returned to the reactor. In a fourth variant, only a portion of the bottoms from the second distillation column is returned to the reactor and the rest is disposed of.

The first and second variants, compared to the third and fourth variants and viewed over the preparation plant, are more energetically favourable and distinctly simpler in apparatus terms. However, more catalyst is lost—which means that more fresh catalyst is required—than in the third and fourth variant; in the first variant because the entire bottoms are disposed of, and in the second variant because it is not possible to return an arbitrarily large amount of water to the reactor and therefore the amount of recyclable catalyst is smaller. However, when the content of catalyst in the bottoms from the first distillation column is so high that the bottoms cannot be released as wastewater into a communal water treatment plant, the second, third and fourth variants are suitable for reducing the amount of problematic wastewater which is discharged compared to the first variant. In the second variant this is accomplished by recycling a portion of the bottoms from the first distillation column into the reactor, in the third variant in that the distillative removal of water enables returning of the entire bottoms from the second distillation column to the reactor and consequently no occurrence of problematic wastewater, and in the fourth variant in that the distillative removal of water and the partial recycling of the bottoms from the second distillation column into the reactor further reduces the amount of problematic wastewater compared to the second variant.

The top stream from the first distillation column is condensed in a condenser. The condensate is separated in a liquid-liquid phase separator into a liquid organic phase containing mainly methacrolein and a liquid aqueous phase. The organic phase is collected in a collecting vessel as product. The aqueous phase is routed back to the first distillation column.

WO 2016/042000 A1 also describes a process in which methacrolein is prepared in a tubular reactor under elevated pressure in the liquid phase from formaldehyde and propionaldehyde in the presence of water and in the presence of a homogeneous catalyst, and the reaction mixture is expanded and routed into a first distillation column. The top stream from the first distillation column is condensed. The condensate is routed into a liquid-liquid phase separator in which a liquid organic phase and a liquid aqueous phase are separated from one another. The organic phase contains methacrolein in such a high concentration that it is removed as product stream. The aqueous phase is wholly or partly returned to the first distillation column. Water and catalyst accumulate in the bottoms from the first distillation column. The bottoms from the first distillation column, apart from a proportion recycled into the first column, are at least partly recycled into the reactor. Any portion not recycled into the reactor is sent to a workup or disposal. The workup can be effected in a second distillation column or in a membrane separation stage. The catalyst is present in elevated concentration in the bottoms from the second distillation column and in the retentate from the membrane separation stage. The bottoms from the second distillation column and the retentate from the membrane separation stage are routed into the reactor.

EP 2829531 A1 discloses a process in which methacrolein is prepared in a tubular reactor under elevated pressure in the liquid phase from formaldehyde and propionaldehyde in the presence of water and in the presence of a homogeneous catalyst, and the reaction mixture is expanded and routed into a distillation column. The top stream from the distillation column is condensed. The condensate is routed into a liquid-liquid phase separator in which a liquid organic phase and a liquid aqueous phase are separated from one another.

The organic phase contains methacrolein in such a high concentration that it is removed as product stream. The aqueous phase is returned to the first distillation column. Water and catalyst accumulate in the bottoms from the first distillation column. A portion of the bottom stream is returned to the reactor. The other portion is sent to a workup by a membrane separation stage. The retentate in which the catalyst is enriched is at least partly recycled into the reactor. The portion of the retentate that has not been recycled is sent to disposal. The permeate as the less contaminated aqueous phase is sent separately to a disposal. In a first modification of the process, two membrane separation stages are provided.

In a second modification of the process, the reaction mixture is significantly cooled and expanded. The significant cooling reduces side reactions and/or the formation of dimethacrolein. This gains time for the further workup of the reaction mixture. The cooled reaction mixture is routed into a liquid-liquid phase separator upstream of the distillation column, in which a liquid organic phase and a liquid aqueous phase are separated from one another. The organic phase is routed into the distillation column, and the aqueous phase wholly or partly into the membrane separation stage. The bottoms from the distillation column can be routed into the liquid-liquid phase separator, into the membrane separation stage or into the reactor, or sent to a disposal.

WO 2018/217961 A1 discloses a process for preparing methacrolein from formaldehyde and propionaldehyde in the presence of water and in the presence of a homogeneous catalyst, in which the reaction is conducted at temperatures of more than 100° C., for example at temperatures of 150-220° C., and elevated pressure in the liquid phase. The reaction mixture containing the homogeneous catalyst is significantly cooled, namely to less than 15° C., preferably to less than 5° C., and then expanded. The significant cooling reduces side reactions and/or the formation of dimethacrolein. This gains time for the further workup of the reaction mixture. The cooled reaction mixture is routed into a first liquid-liquid phase separator in which a liquid organic phase containing a high proportion of methacrolein and a liquid aqueous phase including homogeneous catalyst are separated from one another. Effective separation of water and catalyst thus takes place, with the separating operation in the first liquid-liquid phase separator requiring no energy except for the conveying of liquid. The aqueous phase is routed into a first distillation column. A portion of the bottoms from the first distillation column is returned to the reactor, a further portion is discharged, and the remaining portion is returned to the distillation column.

An aqueous side stream is removed from the first distillation column in order to reduce the water content in the bottoms from the first distillation column. This increases the concentration of the catalyst in the bottoms from the first distillation column, as a result of which, since it is not possible to return an arbitrarily large amount of water to the reactor, the amount of the catalyst returnable to the reactor is increased and the amount or problematic wastewater that has to be disposed of is reduced.

The top stream from the first distillation column is condensed and routed into a second liquid-liquid phase separator in which a liquid organic phase and a liquid aqueous phase are separated from one another. In order to wash out methanol present in the top stream from the first distillation column, the second liquid-liquid phase separator is supplied with additional water. The liquid aqueous phase is discharged. The liquid organic phase from the second liquid-liquid phase separator and the liquid organic phase from the first liquid-liquid phase separator are routed into a second distillation column. The top stream from the second distillation column is condensed and routed into the first liquid-liquid phase separator. The bottoms from the second distillation column containing predominantly methacrolein, apart from a portion routed back into the second distillation column, are routed into a third distillation column. Unwanted organic components are removed via the bottoms from the third distillation column. The top stream from the third distillation column is condensed and contains methacrolein in high purity.

WO2018/217963 A1 discloses a process for preparing methacrolein from formaldehyde and propionaldehyde in the presence of water and in the presence of a homogeneous catalyst, which differs from the process known from WO 2018/217961 A1 particularly in that the top stream from the first distillation column, after being condensed, is not routed into a second liquid-liquid phase separator but discharged as a second product stream.

WO 2018/217964 A1 discloses a process for preparing methacrolein from formaldehyde and propionaldehyde in the presence of water and in the presence of a homogeneous catalyst, which differs from the process known from WO2018/217963 A1 particularly in that the top stream from the second distillation column is not recycled partly into the liquid-liquid phase separator connected upstream of the first and second distillation columns, but discharged completely as the first product stream, and the bottoms from the second distillation column are not routed into a third distillation column, but are a waste stream which is discharged.

WO 2015/065610 A1 discloses a process for preparing methacrolein from formaldehyde and propionaldehyde in the presence of water and in the presence of a homogeneous catalyst, which differs from the process known from WO2018/217963 A1 particularly in that the bottoms from the second distillation column are not routed into a third distillation column, but are discharged directly as a product stream, a portion of the condensed top stream from the second distillation column is returned to the second distillation column, and the top stream from the first distillation column is not removed as the second product stream but routed partly into the first distillation column and into the liquid-liquid phase separator which is connected upstream of the second distillation column and takes the form of a decanter.

The process can be developed in such a way that a portion of the condensed top stream from the second distillation column is routed into a separate decanter and a liquid organic phase removed in this decanter is routed into the second distillation column and/or is added to the bottom stream from the second distillation column. It can also be developed in such a way that a portion of the condensed top stream from the first distillation column is routed into a further separate decanter and a liquid organic phase removed in this decanter is routed into the second distillation column and a liquid aqueous phase removed in this decanter is guided into the first distillation column.

SUMMARY OF THE INVENTION

It is an object of the present invention to provide a process for preparing methacrolein from formaldehyde and propionaldehyde in the presence of water and in the presence of a catalyst based at least on an acid and a base, which can be performed with a good energy balance, in which the amount of problematic wastewater obtained can be minimized and which is implementable with maximum simplicity in apparatus terms. It is a further object of the invention to provide a corresponding preparation plant.

The process object is achieved in accordance with the invention by a process having the features as described below. By virtue of the introducing of the second separation mixture into the second distillation column, the first distillation column is supplied with less water compared to the case if the second separation mixture were to be introduced into the first distillation column. This means that a correspondingly smaller amount of second distillation mixture is obtained, and the second distillation mixture has a correspondingly higher concentration of catalyst. Owing to the higher concentration of catalyst, since the amount of water recyclable into the reactor is limited, more catalyst can be recycled into the reactor, which saves fresh catalyst.

Since a small amount of second distillation mixture is obtained, the amount of problematic wastewater potentially to be disposed of is reduced.

Figure 1:
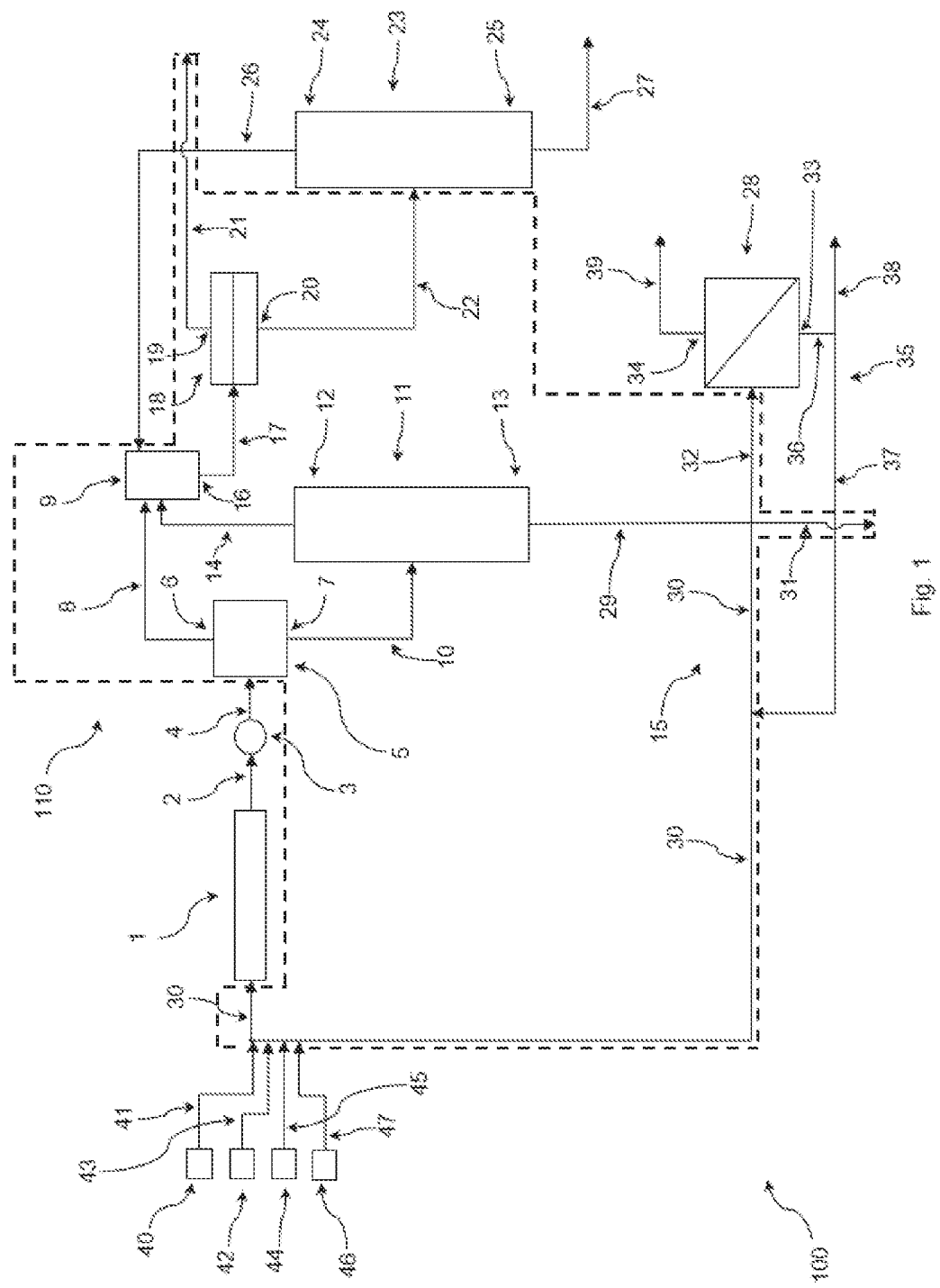
FIG. 1 shows a first embodiment of the invention illustrated by a schematic flow diagram.

By virtue of the introducing of a portion of the second distillation mixture into the reactor, the catalyst present in this portion of the second distillation mixture is utilized again.

By means of the first phase separator, in a simple and effective manner, second separation mixture, and hence a large amount of water, is separated from the first separation mixture which can contain a high proportion of methacrolein.

With the second distillation column, it is still possible to remove a good portion of the methacrolein present in the second separation mixture.

By virtue of the introducing of third distillation mixture into the methacrolein workup plant, the third distillation mixture, which is a methacrolein-containing phase, is sent to a further workup in which the amount of accompanying components is reduced.

The amount of catalyst present in the fourth distillation mixture can be kept small, which is advantageous with regard to the disposal of fourth distillation mixture.

Advantageously, in step S6, at least a portion of the third distillation mixture may be introduced into the first condenser. As a result, no dedicated condenser and phase separator are required for the third distillation mixture, and the apparatus complexity is reduced in that respect. In the first condenser, the third distillation mixture is converted to its condensate, which is routed into the first phase separator.

More preferably, in step S8, at least a portion of the third distillation mixture may be introduced into and condensed in a second condenser that forms part of the methacrolein workup plant, and condensate may be removed from the second condenser and introduced into the first phase separator. The second condenser can condense the third distillation mixture independently of the first condenser. In addition, the second condenser can be utilized for at least partial recycling of third distillation mixture into the second distillation column. By virtue of the introducing of the condensate from the second condenser into the first phase separator, no dedicated phase separator is required for the condensate from the second condenser and the apparatus complexity is reduced in that respect.

Particularly advantageously, in step S8, at least a portion of the third distillation mixture may be introduced into and condensed in a second condenser that forms part of the methacrolein workup plant, condensate may be removed from the second condenser and introduced into a second phase separator that forms part of the methacrolein workup plant and may be separated in the second phase separator into a third separation mixture and a fourth separation mixture, wherein the third separation mixture is in the form of an organic phase comprising methacrolein, and the fourth separation mixture is in the form of an aqueous phase. By virtue of the separation conducted by means of the second phase separator, it is possible to utilize the third separation mixture as a product stream with a good degree of methacrolein workup separate from the first separation mixture, or to combine it with the first separation mixture to give a common product stream with a good degree of methacrolein workup. In other words, the third separation mixture need not necessarily be introduced into the first phase separator.

Moreover, it is especially possible with the second condenser and the second phase separator to return a fraction of the third distillation mixture to the second distillation column, namely the fourth separation mixture, and hence conduct a particularly good separation in the second distillation column, especially a particularly good separation of methacrolein on the one hand and water on the other.

Particularly favourably, in step S6, at least a portion of the third distillation mixture may be introduced into the first distillation column. In this way, the third distillation mixture may be supplied especially to the workup conducted by means of the first distillation column and the first phase separator.

It is preferably possible to
expand the reaction mixture, which gives rise to a first expansion mixture which is the fraction of the reaction mixture that goes into the gas phase as a result of the expansion, and a second expansion mixture which is the fraction of the reaction mixture that remains in the liquid phase,
separate the first and second expansion mixture in an expansion vessel that forms part of the methacrolein workup plant,
introduce the first expansion mixture into the first condenser and
Introduce the second expansion mixture into the first distillation column.

The reaction mixture leaving the reactor is liquid and is under pressure. When it is expanded, the expansion results in conversion of a fraction of the reaction mixture to the gas phase, which gives rise to the first expansion mixture, i.e. the fraction of the reaction mixture that has been converted to the gas phase by the expansion, and the second expansion mixture, i.e. the fraction of the reaction mixture that has remained in the liquid phase. The methacrolein content in the first expansion mixture is higher than in the second expansion mixture. Consequently, the relief of the pressure is already a step for obtaining a mixture having a higher methacrolein content. The first expansion mixture and the second expansion mixture are separated from one another in the expansion vessel.

The relief of the pressure is already accompanied by cooling. There is thus no need for any additional energy expenditure or apparatus complexity for this cooling. In addition, the amount of energy corresponding to the reduction in pressure remains in the system in spite of the cooling associated with the reduction in pressure.

Only the second expansion mixture has to be routed into the first distillation column and heated for the distillation operation. The first expansion mixture is routed straight into the first condenser and condensed therein together with the first distillation mixture coming from the top of the first distillation column.

Favourably, in step S6, at least a portion of the third distillation mixture may be introduced into the expansion vessel. In this way, the third distillation mixture is red via the route via the expansion vessel especially to the workup conducted by means or the first phase separator.

Particularly advantageously, at least a portion of the second distillation mixture removed in step S3.iv may be introduced into a membrane plant, at least a portion of the catalyst present in the second distillation mixture introduced may be retained in the membrane plant, and a retentate mixture comprising the retained catalyst and a permeate mixture may be removed from the membrane plant. Since the retentate mixture has a higher concentration of catalyst than the second distillation mixture and the amount of water returnable into the reactor is limited, more catalyst can be returned to the reactor when retentate mixture is used for the recycling of catalyst into the reactor.

Since the amount of the retentate mixture is smaller than the amount of the second distillation mixture supplied to the membrane plant, the amount of problematic wastewater potentially to be disposed of is reduced if the permeate mixture is not classifiable as problematic wastewater. If the permeate mixture is classifiable as problematic wastewater, the workup thereof is possibly at least simpler, particularly owing to the reduced catalyst content.

The preparation object is achieved in accordance with the invention by a preparation plant having the features as described. By virtue of the second phase separator removal conduit arrangement, it is possible to introduce second separation mixture into the second distillation column. If this is done, the first distillation column is supplied with less water than if this amount of second separation mixture were to be routed into the first distillation column. This means that a correspondingly smaller amount of second distillation mixture is obtained in the first distillation column, and the second distillation mixture has a correspondingly higher concentration of catalyst. Owing to the higher concentration of catalyst, since the amount of water recyclable into the reactor is limited, more catalyst can be recycled into the reactor. Since a small amount of second distillation mixture is obtained, the amount of problematic wastewater potentially to be disposed of is reduced.

By means of the first phase separator. In a simple and effective manner, second separation mixture, and hence a large amount of water, is separated from the first separation mixture which can contain a high proportion of methacrolein.

With the second distillation column, it is still possible to remove a good portion of the methacrolein present in the second separation mixture.

By virtue of the third distillation column removal conduit arrangement, it is possible to route third distillation mixture into the methacrolein workup plant. This means that the third distillation mixture, which is a methacrolein-containing phase, can be sent to a further workup in which the amount of accompanying components is reduced.

Since the second distillation column can be supplied with second separation mixture wherein the amount of catalyst is small, the amount of catalyst present in the fourth distillation mixture is small. This is advantageous with regard to the disposal of fourth distillation mixture.

Advantageously, the third distillation column removal conduit arrangement may fluidically connect the top of the second distillation column to the first condenser, and third distillation mixture may be routed through the third distillation column removal conduit arrangement from the top of the second distillation column into the first condenser. Since third distillation mixture can be introduced into the first condenser, no dedicated condenser and phase separator are required for the third distillation mixture, and the apparatus complexity is reduced in that respect. In the first condenser, the third distillation mixture is converted to its condensate, which can be routed into the first phase separator.

Preferably,
the preparation plant may have a second condenser that forms part of the methacrolein workup plant,
the third distillation column removal conduit arrangement may fluidically connect the top of the second distillation column to the second condenser, wherein third distillation mixture may be routed through the third distillation column removal conduit arrangement from the top of the second distillation column into the second condenser and condensed in the second condenser, and
the second condenser may be fluidically connected to the first phase separator, by means of which condensate from the second condenser may be routed from the second condenser further into the first phase separator.

The second condenser can condense the third distillation mixture independently of the first condenser. In addition, the second condenser can be utilized for at least partial recycling of third distillation mixture into the second distillation column.

Moreover, this setup does not require a dedicated phase separator for the condensed distillation mixture. Apparatus complexity is reduced in that respect.

More preferably,
the preparation plant may have a second condenser that forms part of the methacrolein workup plant,
the third distillation column removal conduit arrangement may fluidically connect the top of the second distillation column to the second condenser, wherein third distillation mixture may be routed through the third distillation column removal conduit arrangement from the top of the second distillation column into the second condenser and condensed in the second condenser, and
the second condenser may be fluidically connected to a second phase separator that forms part of the methacrolein workup plant, by means of which condensate from the second condenser may be routed from the second condenser further into the second phase separator, with which a third separation mixture of organic phase present in the condensate supplied by the second condenser may be separated from a fourth separation mixture or aqueous phase present in the condensate supplied by the second condenser, wherein the second phase separator has a first outlet for removal of third separation mixture and a second outlet for removal of fourth separation mixture.

With this setup, it is possible to introduce at least a portion of the third distillation mixture into the second condenser and condense it therein, remove condensate from the second condenser and introduce it into the second phase separator in which the third separation mixture and the fourth separation mixture can be separated. By virtue of the separation conducted by the second phase separator, it is possible to utilize the third separation mixture as a product stream with a good degree of methacrolein workup separate from the first separation mixture, or to combine it with the first separation mixture to give a common product stream with a good degree of methacrolein workup. In other words, the third separation mixture need not necessarily be introduced into the first phase separator. Moreover, it is especially possible with the second condenser and the second phase separator to return a fraction of the third distillation mixture to the second distillation column, namely the fourth separation mixture, and hence conduct a particularly good separation in the second distillation column, especially a good separation of methacrolein on the one hand and water on the other.

Particularly advantageously, the third distillation column removal conduit arrangement may fluidically connect the top of the second distillation column to the first distillation column, and third distillation mixture may be routed through the third distillation column removal conduit arrangement from the top of the second distillation column into the first distillation column. In this way, third distillation mixture can especially be supplied to the workup conducted with the first phase separator.

Preferably, the methacrolein workup plant may include an expansion vessel with which a first expansion mixture which is the fraction of the reaction mixture that goes into the gas phase as a result of expansion of the reaction mixture and a second expansion mixture which is the fraction of the reaction mixture remaining in the liquid phase after the expansion of the reaction mixture may be separated from one another, wherein the expansion vessel has a first outlet for removal of first expansion mixture which is fluidically connected to the first condenser, by means of which first expansion mixture may be routed into the first condenser, and a second outlet for removal of second expansion mixture which is fluidically connected to the first distillation column, by means of which second expansion mixture may be routed into the first distillation column.

The reaction mixture leaving the reactor is liquid and is under pressure. When it is expanded, the expansion results in conversion of a fraction of the reaction mixture to the gas phase, which gives rise to the first expansion mixture. i.e. the fraction of the reaction mixture that has been converted to the gas phase by the expansion, and the second expansion mixture, i.e. the fraction of the reaction mixture that has remained in the liquid phase. The methacrolein content in the first expansion mixture is higher than in the second expansion mixture. Consequently, the relief of the pressure is already a step for obtaining a mixture having a higher methacrolein content. The expansion vessel can separate the first and second expansion mixture from one another, and both can be removed separately from the expansion vessel. By virtue of the first outlet being fluidically connected to the first condenser, it is possible to route first expansion mixture into the first condenser. It can be condensed there together with the first distillation mixture coming from the top of the first distillation column. By virtue of the second outlet being fluidically connected to the first distillation column, second expansion mixture can be routed into the first distillation column—only the second expansion mixture has to be routed into the first distillation column and accordingly heated for the distillation operation.

Favourably, the third distillation column removal conduit arrangement may fluidically connect the top of the second distillation column to the expansion vessel, and third distillation mixture may be routed through the third distillation column removal conduit arrangement from the top of the second distillation column into the expansion vessel. As a result, the third distillation mixture may be fed via the route via the expansion vessel especially to the workup conducted by means of the first phase separator.

Advantageously, the bottom of the first distillation column may be fluidically connected to the reactor, by means of which second distillation mixture can be routed into the reactor. This setup allows catalyst present in the second distillation mixture to be utilized again.

Preferably, the production plant may include a membrane plant which is fluidically connected to the bottom of the first distillation column, and with which at least a portion of catalyst present in second distillation mixture fed to the membrane plant can be retained, and the membrane plant may have a first outlet for removal of retentate mixture containing the catalyst retained and a second outlet for removal of permeate mixture. With the aid of the membrane plant, it becomes possible to return more catalyst to the reactor. This is because the amount or water returnable to the reactor is limited. The retentate mixture has a higher concentration of catalyst than the second distillation mixture and can be used for the recycling of catalyst into the reactor.

Moreover, the use of the membrane plant allows the amount of problematic wastewater potentially to be disposed of to be reduced if the permeate mixture is not classifiable as problematic wastewater. This is because the amount of the retentate mixture is smaller than the amount of the second distillation mixture supplied to the membrane plant. If the permeate mixture is classifiable as problematic wastewater, the workup thereof is possibly at least simpler, particularly owing to the reduced catalyst content.

More preferably, the production plant. In all variants possible with the possible configurations described, may be used for preparation of methacrolein, especially for preparation of methacrolein from formaldehyde and propionaldehyde in the presence of water and in the presence of a homogeneous catalyst based at least on an acid and a base.

Figure 2:
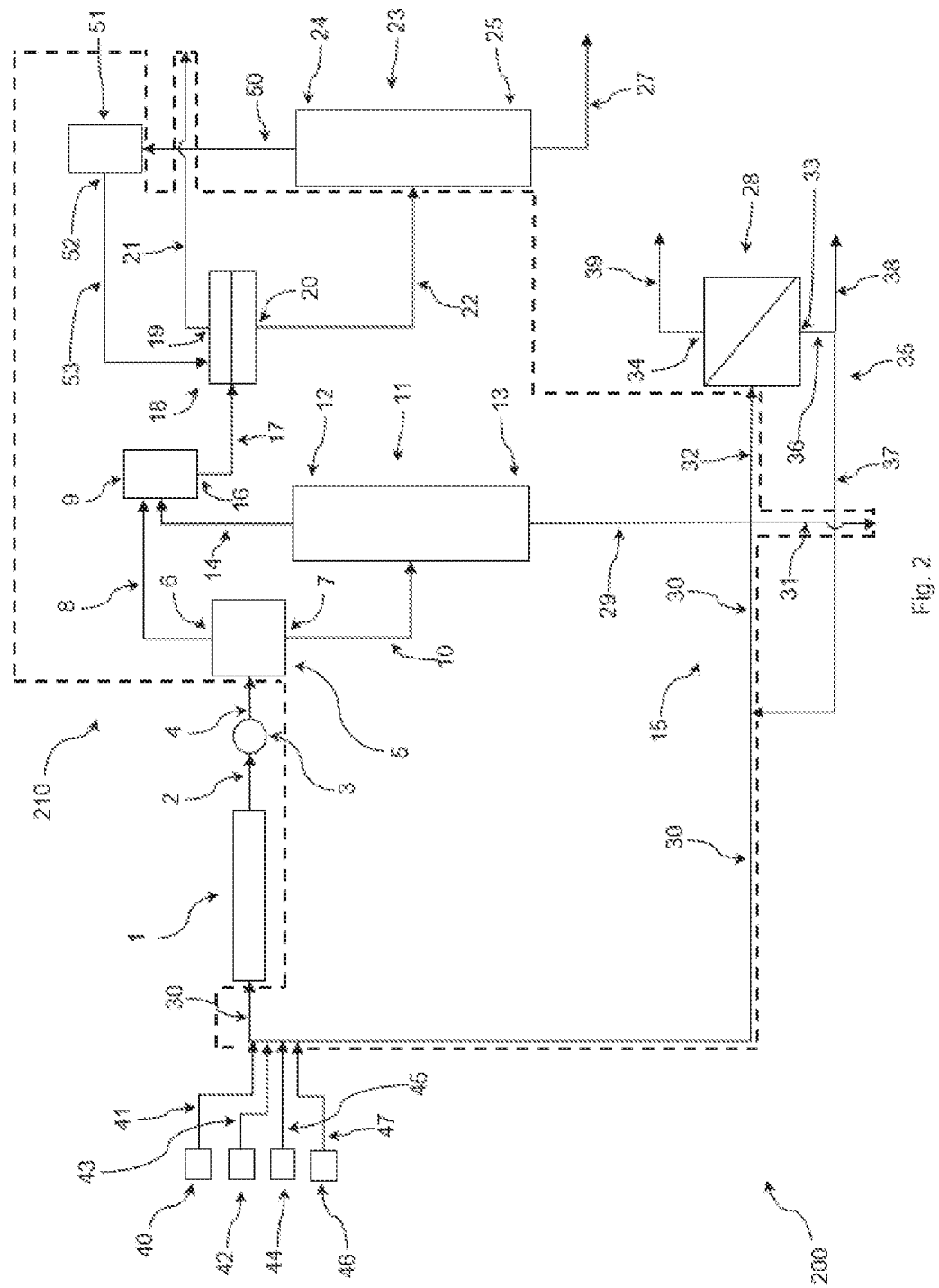
FIG. 2 shows a second embodiment of the invention illustrated by a schematic flow diagram.
Figure 3:
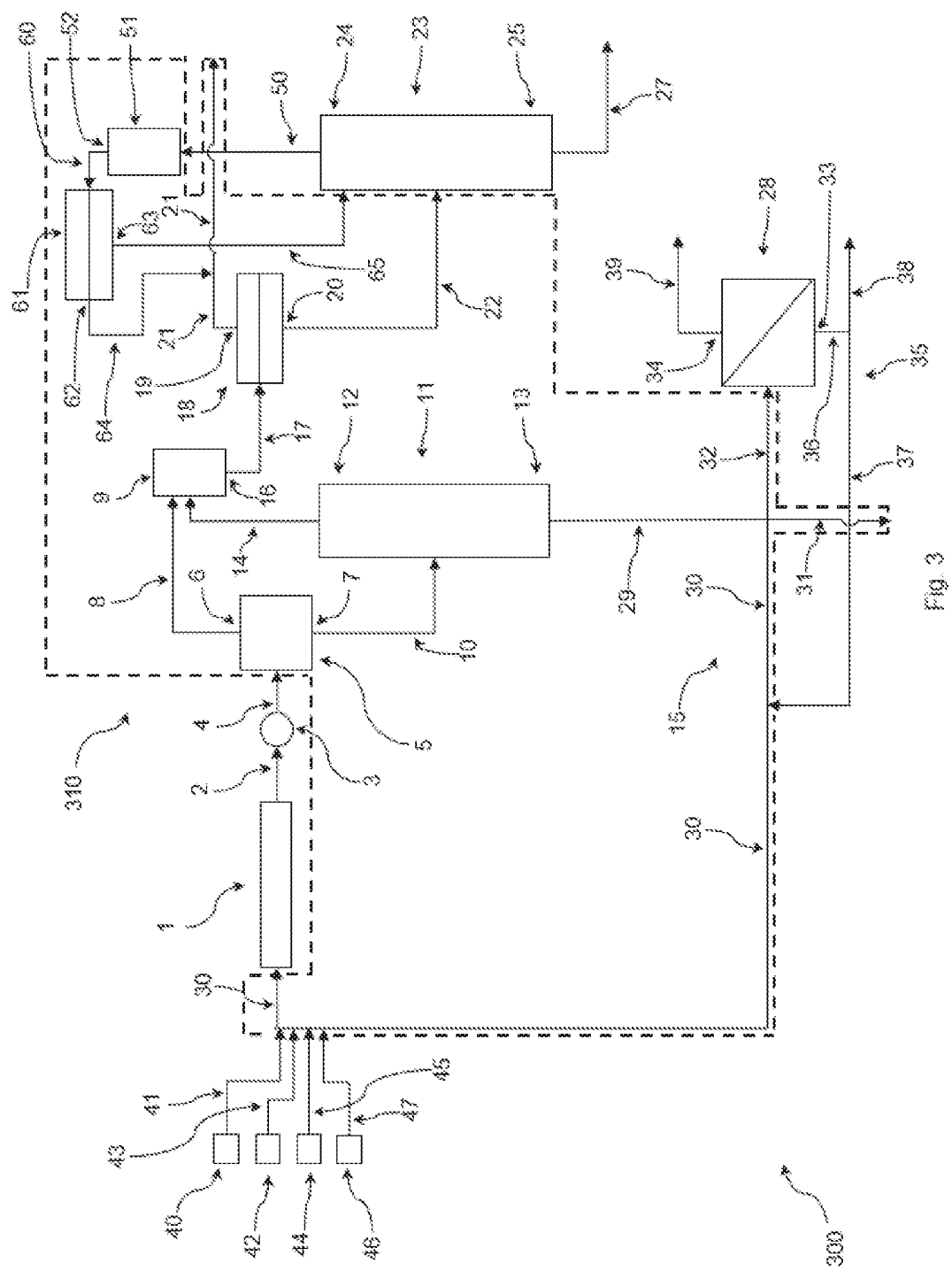
FIG. 3 shows a third embodiment of the invention illustrated by a schematic flow diagram.
Figure 4:
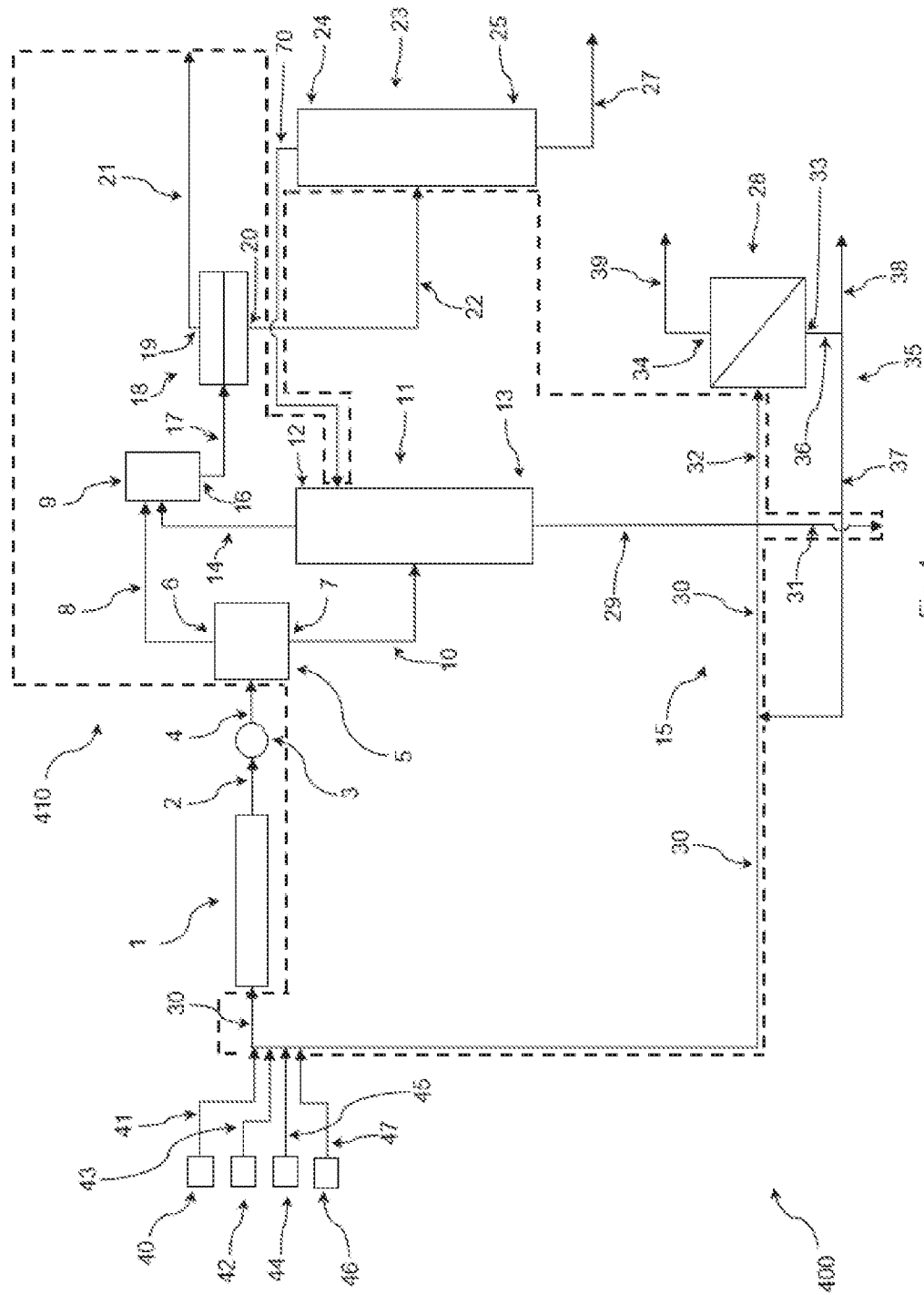
FIG. 4 shows a fourth embodiment of the invention illustrated by a schematic flow diagram.
Figure 5:
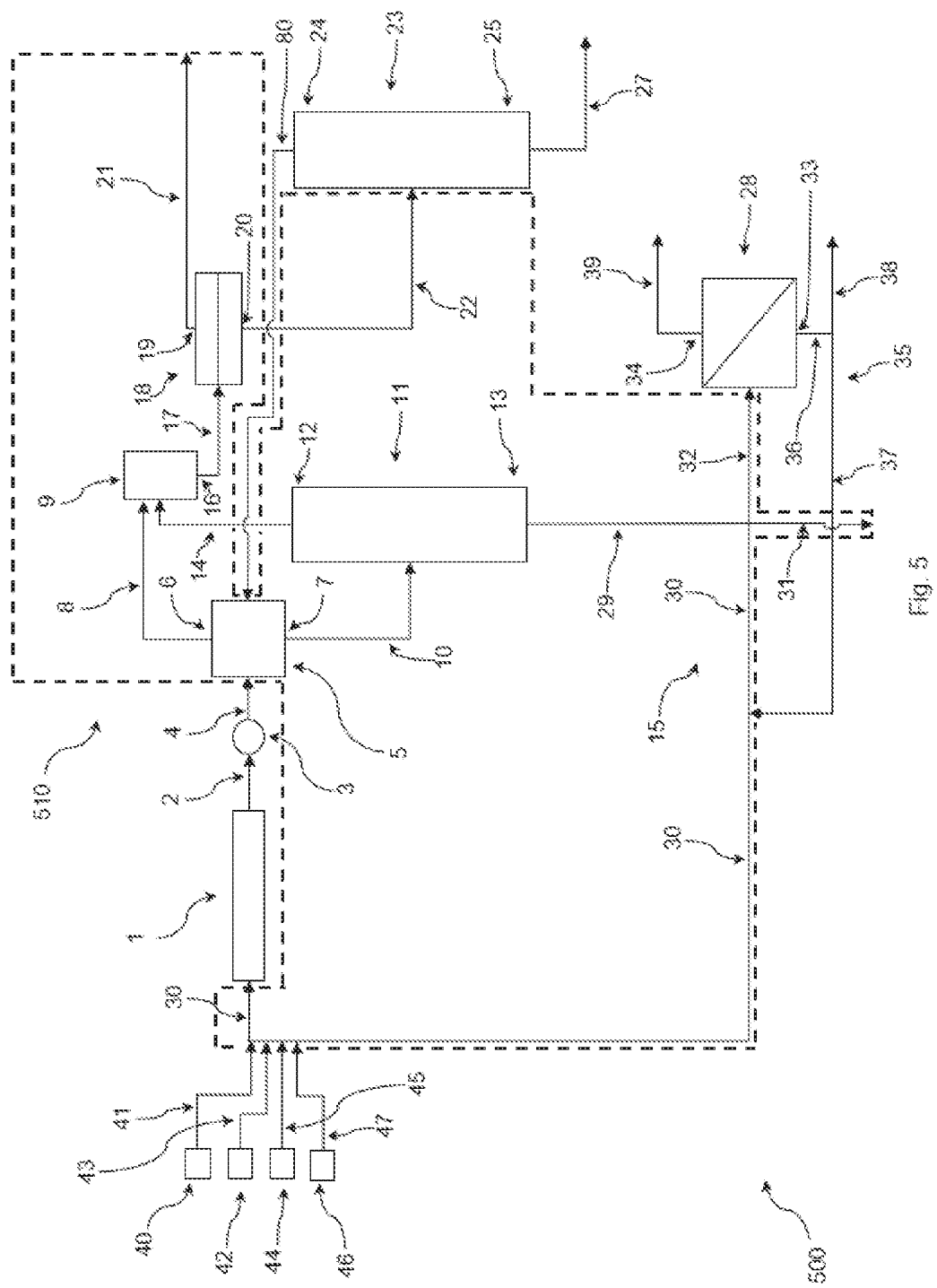
FIG. 5 shows a fifth embodiment of the invention illustrated by a schematic flow diagram.

The figures show some possible embodiments of the present invention. The figures show:

FIG. 1 a first embodiment of the invention illustrated by a schematic flow diagram, FIG. 2 a second embodiment of the invention illustrated by a schematic flow diagram, FIG. 3 a third embodiment of the invention illustrated by a schematic flow diagram, FIG. 4 a fourth embodiment of the invention illustrated by a schematic flow diagram, FIG. 5 a fifth embodiment of the invention illustrated by a schematic flow diagram.

Figure 6:
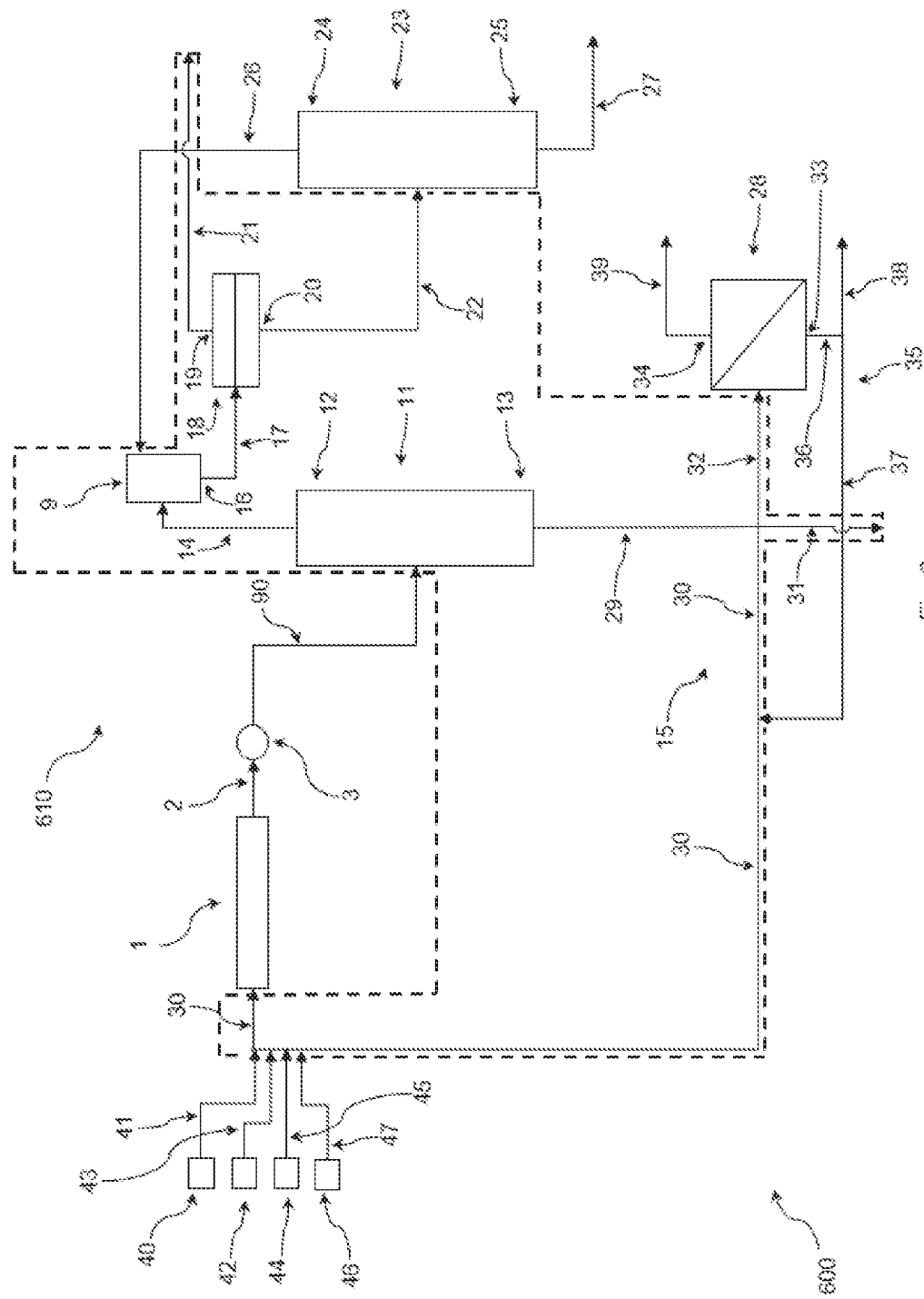
FIG. 6 shows a sixth embodiment of the invention illustrated by a schematic flow diagram.
Figure 7:
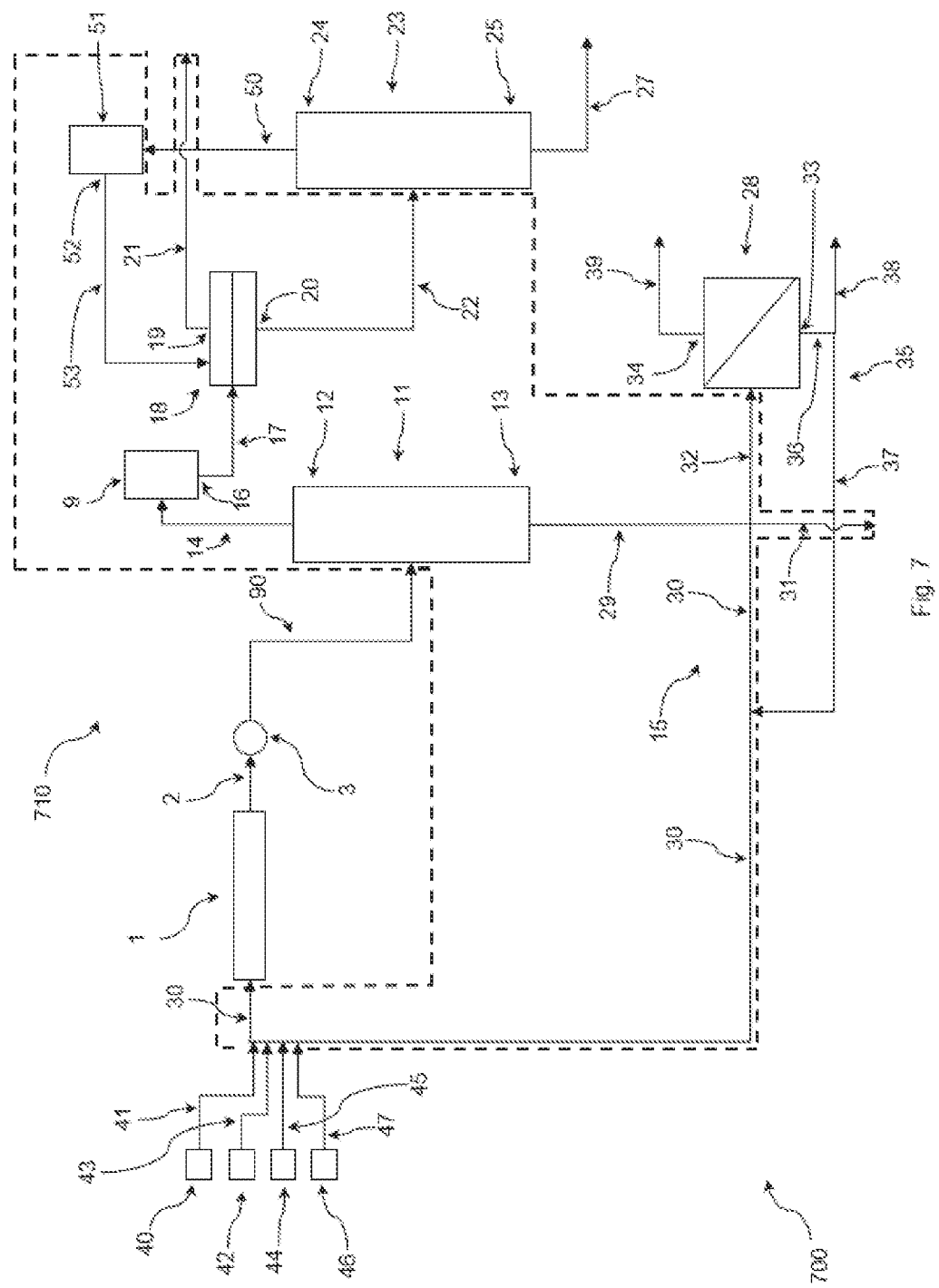
FIG. 7 shows a seventh embodiment of the invention illustrated by a schematic flow diagram.
Figure 8:
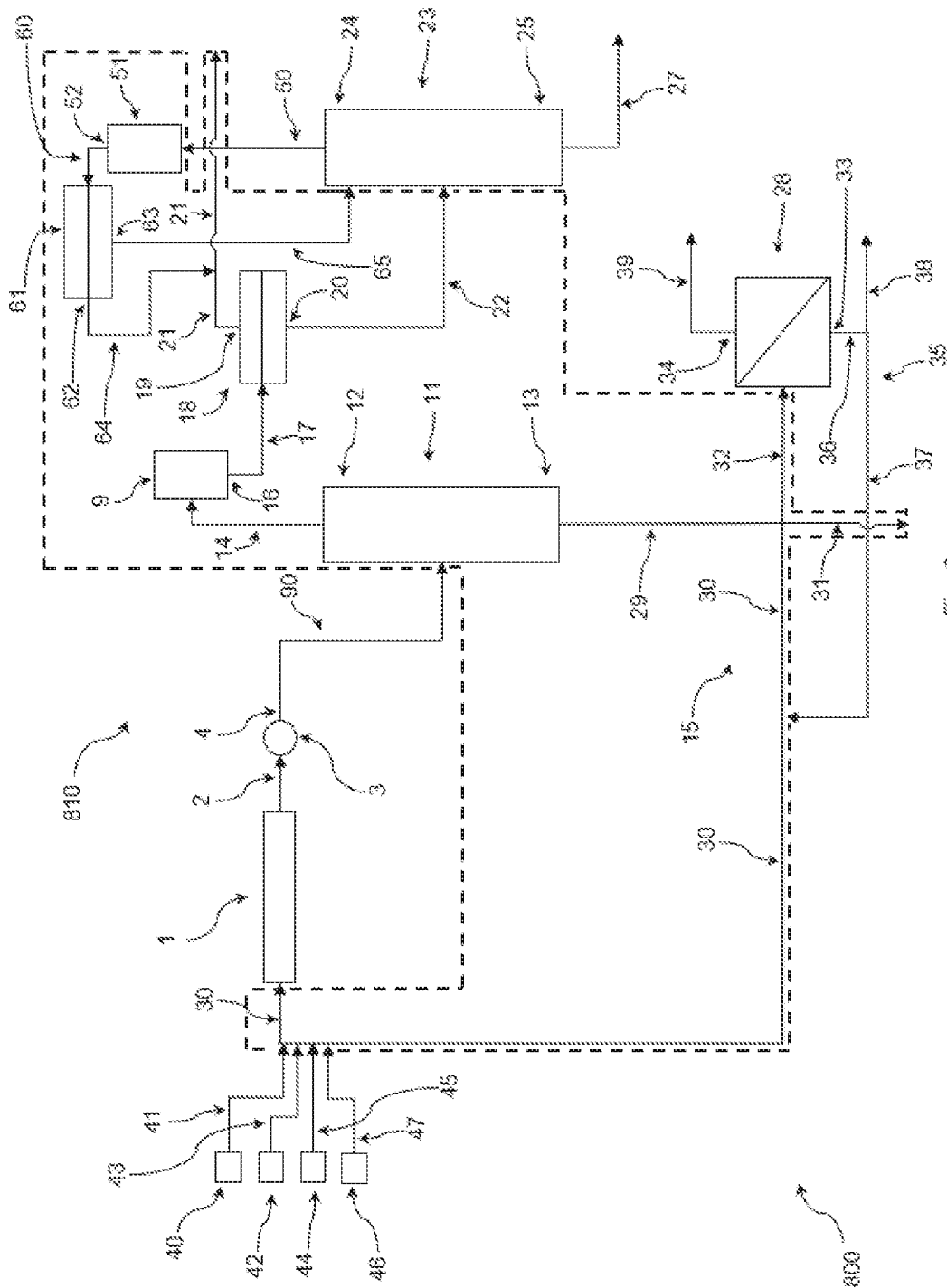
FIG. 8 shows an eighth embodiment of the invention illustrated by a schematic flow diagram.
Figure 9:
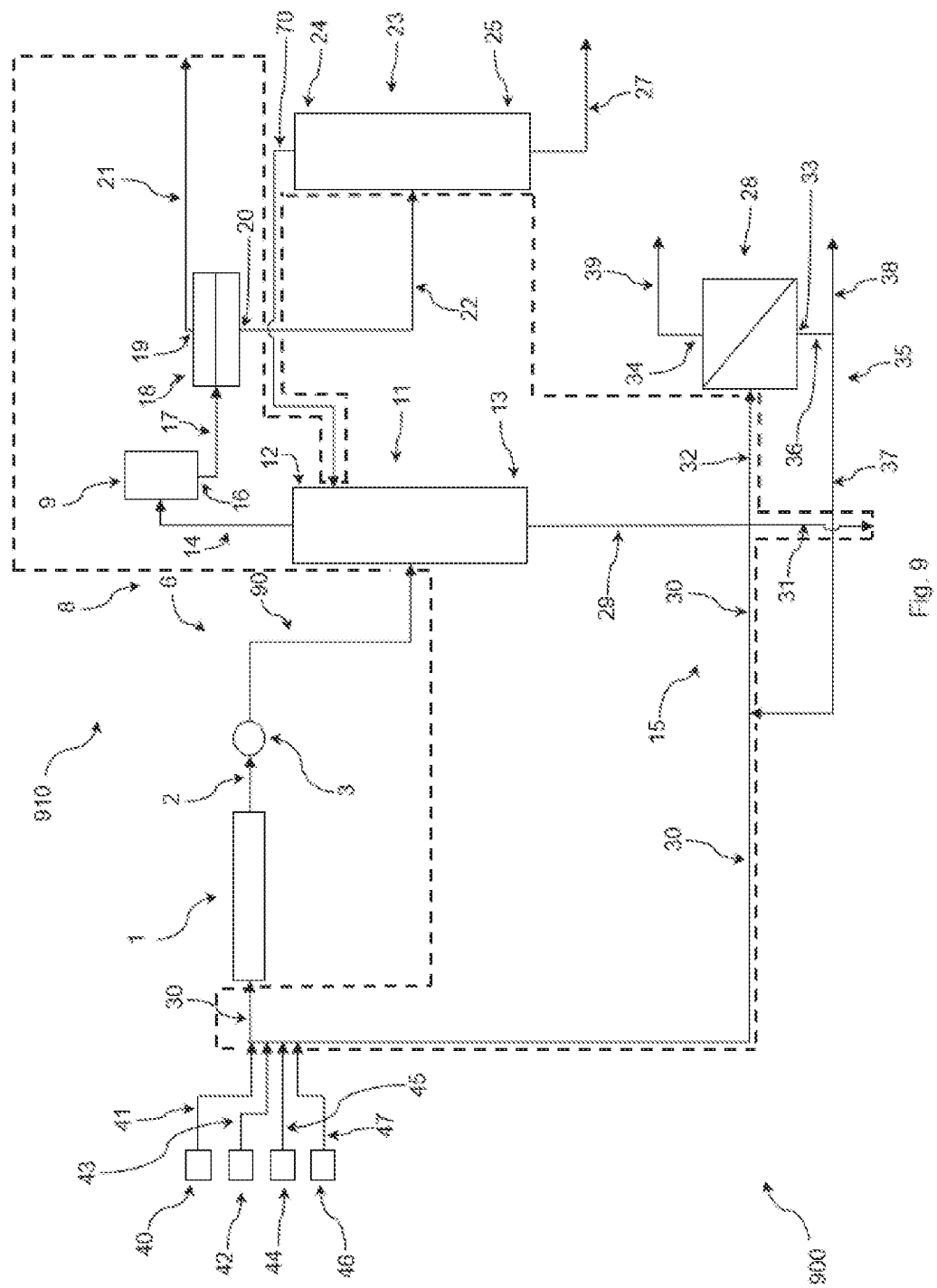
FIG. 9 shows a ninth embodiment of the invention illustrated by a schematic flow diagram.

FIG. 6 a sixth embodiment of the invention illustrated by a schematic flow diagram, FIG. 7 a seventh embodiment of the invention illustrated by a schematic flow diagram, FIG. 8 an eighth embodiment of the invention illustrated by a schematic flow diagram and FIG. 9 a ninth embodiment of the invention illustrated by a schematic flow diagram.

In the schematic flow diagrams in FIGS. 1 to 9, the arrows indicate the flow direction of the respective medium in the course of performance of the process in question. If the arrows were omitted. FIGS. 1 to 9 would be schematic diagrams of the preparation plants of the first to ninth embodiments of the invention.

In FIGS. 1 to 9, dotted lines indicate which part of the respective preparation plant forms part of the methacrolein workup plant of this preparation plant.

Reference is made to FIG. 1. The preparation plant 100 of the first embodiment of the invention Illustrated therein has a reactor 1 in which a reaction can be conducted in the liquid phase under elevated pressure, in which methacrolein is formed from formaldehyde and propionaldehyde in the presence of water and in the presence of a homogeneous catalyst based at least on an acid and a base. A reactor removal conduit arrangement 2 fluidically connects the reactor 1 to an expansion valve 3, by means of which reaction mixture can be routed from the reactor 1 through the reactor removal conduit arrangement 2 to the expansion valve 3. The expansion valve 3 can expand reaction mixture under elevated pressure coming from the reactor 1 to a lower pressure, and the expansion valve 3 can simultaneously regulate the pressure in the reactor 1. The expansion valve 3 could also be described as a pressure-retaining and expansion valve.

The expansion valve 3 is fluidically connected to a methacrolein workup plant 110 with which the proportion accounted for by accompanying components, for example water, catalyst, unconverted formaldehyde and unconverted propionaldehyde, in the reaction mixture or in a fraction of the reaction mixture can be reduced. The methacrolein workup plant 110 includes an expansion vessel 5. The expansion valve 3 is fluidically connected thereto via an expansion valve removal conduit arrangement 4. The expansion vessel 5 can be used to separate a first expansion mixture which is the fraction of the reaction mixture that goes into the gas phase as a result of an expansion of reaction mixture, and a second expansion mixture which is the fraction of the reaction mixture that remains in the liquid phase after the expansion of the reaction mixture. The expansion vessel 5 may also be referred to as an expansion drum, although it need not have the shape of a drum, or as a flashbox.

The expansion vessel 5 has a first outlet 6 for removal of first expansion mixture and a second outlet 7 for removal of second expansion mixture.

The methacrolein workup plant 110 also has a first condenser 9. The first outlet 6 of the expansion vessel 5 is fluidically connected to the first condenser 9 via a first expansion vessel removal conduit arrangement 8, by means of which first expansion mixture can be routed from the expansion vessel into the first condenser 9. The first condenser 9 can be used to condense first expansion mixture.

The methacrolein workup plant 110 also has a first distillation column 11 having a top 12 and a bottom 13. The second outlet 7 of the expansion vessel 5 is fluidically connected to the second distillation column 11 via a second expansion vessel removal conduit arrangement 10, it being possible to route second expansion mixture through the second expansion vessel removal conduit arrangement 10 from the expansion vessel 5 into the first distillation column 11. The first distillation column 11 can be used to separate second expansion mixture into a first distillation mixture in the form of a gas phase, containing methacrolein, and a second distillation mixture in the form of a liquid phase, containing water and catalyst.

By means of a first distillation column removal conduit arrangement 14, the top 12 of the first distillation column 11 is fluidically connected to the first condenser 9. The first distillation column removal conduit arrangement 14 can route first distillation mixture from the top 12 of the first distillation column 11 into the first condenser 9. The first distillation mixture supplied can be condensed in the first condenser 9.

The first expansion vessel removal conduit arrangement 8 and the first distillation column removal conduit arrangement 14 are each connected to a dedicated inlet of the first condenser 9.

The bottom 13 of the first distillation column 11 is fluidically connected to the reactor 1 by a second distillation column removal conduit arrangement 15. The second distillation column removal conduit arrangement 15 can route second distillation mixture from the first distillation column 11 into the reactor 1.

The methacrolein workup plant 110 also has a first phase separator 18. The first phase separator 18 is fluidically connected via a condenser removal conduit arrangement 17 to a condensate outlet 18 of the first condenser 9. The condenser removal conduit arrangement 17 can route condensate from the first condenser 9 from the first condenser 9 into the first phase separator 18. The first phase separator 18 can separate a first separation mixture of organic phase present in the condensate from the first condenser 9 from a second separation mixture of aqueous phase present in the condensate from the first condenser 9. The first phase separator 18 has a first outlet 19 for removal of first separation mixture and a second outlet 20 for removal of second separation mixture. By means of a first phase separator removal conduit arrangement 21 fluidically connected to the first outlet 19 of the first phase separator 18, first separation mixture can be removed from the first phase separator 18. By means of a second phase separator removal conduit arrangement 22 fluidically connected to the second outlet 20, second separation mixture can be removed from the first phase separator 18.

The preparation plant 100 also has a second distillation column 23 having a top 24 and a bottom 25. The second distillation column 23 is not part of the methacrolein workup plant 110. The second phase separator removal conduit arrangement 22 fluidically connects the second outlet 20 of the first phase separator 18 to the second distillation column 23. The second phase separator removal conduit arrangement 22 can route second separation mixture from the second outlet of the first phase separator 18 into the second distillation column 23. The second distillation column 23 can separate second separation mixture at least into a methacrolein-containing third distillation mixture in the form of a gas phase and a water-containing fourth distillation mixture in the form of a liquid phase.

A third distillation column removal conduit arrangement 28 is fluidically connected to the top 24 of the second distillation column 23. The third distillation column removal conduit arrangement 26 fluidically connects the top 24 of the second distillation column 23 to the methacrolein workup plant 110, it being possible to route third distillation mixture through the third distillation column removal conduit arrangement 26 from the top 24 of the second distillation column 23 into the expansion vessel 110. The third distillation column removal conduit arrangement 28 fluidically connects the top 24 of the second distillation column 23 to the first condenser 9, it being possible to route third distillation mixture through the third distillation column removal conduit arrangement 28 from the top 24 of the second distillation column 23 into the first condenser 9.

The third distillation column removal arrangement 28 is connected to a dedicated inlet of the first condenser 9.

By means of a fourth distillation column removal conduit arrangement 27 fluidically connected to the bottom 25 of the second distillation column 23, fourth distillation mixture can be removed from the second distillation column 23.

The preparation plant 100 has a membrane plant 28 fluidically connected to the bottom 13 of the distillation column 11. The membrane plant 28 is fluidically connected to the bottom 13 of the first distillation column 11 by the second distillation column removal conduit arrangement 15, it being possible to route second distillation mixture through the second distillation column removal conduit arrangement 15 from the bottom 13 of the first distillation column 11 into a membrane plant 28.

The second distillation column removal conduit arrangement 15 can also remove second separation mixture from the preparation plant 100.

The second distillation column removal arrangement 15 of the embodiment shown in FIG. 1 has a first section 29, a second section 30, a third section 31 and a fourth section 32. The first section 29 is fluidically connected firstly to the bottom 13 of the first distillation column 11, and secondly to the second section 30, the third section 31 and the fourth section 32.

The second section 30 is fluidically connected to the reactor 1, by means of which second distillation mixture can be routed from the bottom 13 of the first distillation column 11 through the first and second sections 29, 30 of the second distillation column removal conduit arrangement 15 from the bottom 13 of the first distillation column 11 into the reactor 1.

By means of the first and third sections 29, 31 of the second distillation column removal conduit arrangement 15, it is possible to remove second distillation mixture from the preparation plant 100. The fourth section 32 is fluidically connected to the membrane plant 28, by means of which second distillation mixture can be routed through the first and fourth sections 29, 32 of the second distillation column removal conduit arrangement 15 from the bottom 13 of the first distillation column 11 into the membrane plant 28.

The membrane plant 28 can retain at least a portion of the catalyst present in the second distillation mixture fed to the membrane plant 28. The membrane plant 28 has a first outlet 33 for removal of retentate mixture containing the retained catalyst, and a second outlet 34 for removal of permeate mixture. The first outlet 33 is fluidically connected to a first membrane plant removal conduit arrangement 35, by means of which retentate mixture can be removed from the membrane plant 28 via the first outlet 33 from the membrane plant 28.

In the working example shown in FIG. 1, the first membrane plant removal conduit arrangement has a first section 38, a second section 37 and a third section 38. The first section 38 is fluidically connected firstly to the first outlet 33 of the membrane plant 28 and secondly to the second section 37 and the third section 38 of the first membrane plant removal conduit arrangement 35. The second section 37 of the first membrane plant removal conduit arrangement 35 is fluidically connected to the second section 30 of the second distillation column removal conduit arrangement 15, by means of which retentate mixture may be routed from the membrane plant 28 via the first outlet 33 thereof and the first and second sections 36, 37 of the first membrane plant removal conduit arrangement 35 into the second section 30 of the second distillation column removal conduit arrangement 15, and further through the latter into the reactor 1.

The first and third sections 38, 38 of the first membrane plant removal conduit arrangement 35 can remove retentate mixture from the preparation plant 100.

A second membrane plant removal conduit arrangement 39 is fluidically connected to the second outlet 34 of the membrane plant 28, it being possible to discharge permeate mixture from the second outlet 34 of the membrane plant 28 through the second membrane plant removal conduit arrangement 39 from the preparation plant 100.

In the embodiment of the present invention shown in FIG. 1, a formaldehyde source 40 is fluidically connected via a formaldehyde feed arrangement 41 to the second distillation column removal conduit arrangement 15, by means of which formaldehyde can be routed through the formaldehyde feed arrangement 41 into the second distillation column removal conduit arrangement 15, and further through the latter into the reactor 1. A propionaldehyde source 42 is fluidically connected via a propionaldehyde feed arrangement 43 to the second distillation column removal conduit arrangement 15, by means of which propionaldehyde can be routed from the propionaldehyde source 42 through the propionaldehyde feed arrangement 43 into the second distillation column removal conduit arrangement 15, and further through the latter into the reactor 1. A base source 44 is fluidically connected via a base feed arrangement 45 to the second distillation column removal conduit arrangement 15, by means of which a base or bases can be routed through the base feed arrangement 45 into the second distillation column removal conduit arrangement 15, and further through the latter into the reactor 1. An acid source 46 is fluidically connected via an acid feed arrangement 47 to the second distillation column removal conduit arrangement 15, by means of which acid or acids can be routed through the acid feed arrangement 47 into the second distillation column removal conduit arrangement 15, and further through the latter into the reactor 1.

The preparation plant 100 can be used, for example, to perform the process described hereinafter for preparation of methacrolein from formaldehyde and propionaldehyde in the presence of water and a homogeneous catalyst based at least on an acid and a base.

Formaldehyde, propionaldehyde, water and homogeneous catalysts are introduced into the reactor 1 through the second section 30 of the second distillation column removal conduit arrangement 15. Fresh formaldehyde is Introduced here from the formaldehyde source 40 via the formaldehyde feed conduit 41 into the second section 30 of the second distillation column removal conduit arrangement 15, fresh propionaldehyde from the propionaldehyde source 42 via the propionaldehyde feed arrangement 43, one or more fresh bases from the base source 44 via the base feed arrangement 45, and one or more fresh acids from the acid source 46 via the acid feed arrangement 47. The formaldehyde, the acid or acids and the base or bases are each in an aqueous solution, i.e. these aqueous solutions introduce water. The acid or acids in conjunction with the base or bases are the homogeneous catalyst.

Suitable aqueous formaldehyde solutions are, for example, those having a content based on the total mass of the formaldehyde solution of 30% to 55% by weight of formaldehyde with a preferably low methanol content of, for example, 0.3% to 10% by weight, based on the total mass of the formaldehyde solution.

Propionaldehyde is available in highly concentrated form. For example, propionaldehyde feedstock mixture is available with a residual water content of 0.1% to 2.5% by weight, based on the total mass of the propionaldehyde feedstock mixture, and a propionic acid content of 0.01% to 1% by weight, based on the total mass or the propionaldehyde feedstock mixture.

Preference is given to a slight excess of formaldehyde over propionaldehyde in the reactor input. Particular preference is given to choosing a molar ratio of formaldehyde to propionaldehyde in the reactor inlet in the range from 0.90 to 0.99, most preferably 0.95 to 0.98. In this way, it is firstly possible to achieve a good conversion with low formaldehyde consumption. Secondly, the catalyst is also protected at the same time. This is because excessively high formaldehyde contents promote the conversion of dimethylamine to trimethylamine.

Suitable acids are especially inorganic acids, organic monocarboxylic acids, organic dicarboxylic acids and organic polycarboxylic acids. Other organic acids are also usable in principle, but are not usually used for reasons of cost. Preference is given to using organic monocarboxylic acids.

Inorganic acids used may, for example, be sulfuric acid and/or phosphoric acid.

Of the organic monocarboxylic acids, preference is given to aliphatic organic monocarboxylic acids. Of the aliphatic monocarboxylic acids, preference is given to those having two to ten carbon atoms, particularly those having two, three or four carbon atoms.

Of the aliphatic dl- and polycarboxylic acids, preference is given to those having two to ten carbon atoms, particularly those having two, four, five or six carbon atoms.

The organic dicarboxylic acids and the organic polycarboxylic acids may be aromatic, araliphatic and aliphatic carboxylic acids, preference being given to aliphatic di- and polycarboxylic acids.

For example, it is possible to use acetic acid, propionic acid, methoxyacetic acid, n-butyric acid, isobutyric acid, oxalic acid, succinic acid, tartaric acid, glutaric acid, adipic acid, maleic acid or fumaric acid, preference being given to acetic acid.

It is also possible to use mixtures of two or more acids.

Suitable bases are especially organic bases, preference being given to amines.

Of the amines, preference is given to secondary amines, particularly those of the formula $R^1R^2NH$ in which $R^1$ and $R^2$
- may be the same or different and
- may each denote:
  - an alkyl radical having one to ten carbon atoms, preferably one to eight carbon atoms, more preferably one to four carbon atoms, where the carbon atoms may also be substituted by ether, hydroxy or secondary or tertiary amine groups, preferably by one or two of these groups.
  - an aralkyl radical having seven to twelve carbon atoms, a cycloalkyl radical having five to seven carbon atoms, together with the adjacent nitrogen members of a heterocyclic ring, preferably of a five- to seven-membered ring, that may also contain a further nitrogen atom and/or an oxygen atom and may be substituted by hydroxyalkyl or alkyl groups having one to four carbon atoms.

It Is possible to use one or more bases.

Amines used may be, for example: dimethylamine, diethylamine, methylethylamine, methylpropylamine, dipropylamine, dibutylamine, diisopropylamine, diisobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine or dicyclohexylamine.

It is also possible to use mixtures of two or more bases.

If a mixture of amines is used, the amines are preferably selected such that at least one of the amines used does not have a hydroxy group. More preferably, the proportion of amines having at least one hydroxy group in the reactor is not more than 50% by weight, preferably not more than 30% by weight and more preferably not more than 10% by weight, based on the weight of amines used.

The proportion of acid or acids (in total) based on propionaldehyde in the reactor is preferably in the range from 0.1 to 20 mot %, more preferably in the range from 0.5 to 10 mol % and most preferably in the range from 1 to 5 mol %. In the case of too small an amount of acid—and hence too small an amount of catalyst—in the reactor, the reactor would have to be constructed quite large and operated quite hot. In the case of too large an amount of acid—and hence too large an amount of catalyst—the reactor would become quite hot.

It is advisable to have somewhat more acid compared to the base in the reactor. This is advantageous since the Mannich reaction requires protons. Acids can also bind bases. If, for example, the acid chosen is acetic acid and the base chosen is dimethylamine, the acetic acid binds the volatile dimethylamine. This prevents dimethylamine as volatile component from getting into the tops from the first distillation column 11.

If, for example, the acid chosen is acetic acid and the base dimethylamine, a molar ratio of acetic acid to dimethylamine in the range from 2.0 to 1.1 at the reactor inlet is of good suitability, particular preference being given to a molar ratio of acetic acid to dimethylamine of 1.1.

The proportion of the base or bases (in total) based on propionaldehyde in the reactor inlet is preferably in the range from 0.1 to 20 mol % based on moles of propionaldehyde at the reactor inlet, more preferably in the range from 0.5 to 15 mol % based on moles of propionaldehyde at the reactor inlet, and most preferably in the range from 1 to 10 mol % based on moles of propionaldehyde at the reactor inlet. If too small an amount of base or bases is used, the reaction is unselective and the reactor has to be operated at higher temperatures. If too large an amount of base or bases is used, the performance of the reaction becomes increasingly uneconomic, and the wastewater is found to be even more highly polluted.

If the base used is dimethylamine, for example, the molar ratio of dimethylamine to propionaldehyde in the reactor inlet is preferably in the range from 0.08 to 0.12, more preferably 0.08 to 0.1.

Preference is given to a stoichiometric ratio of acid to base of greater than one in order to have sufficient acidity to cleave the Mannich base, especially when a volatile base able to efficiently bind the base is used, in order to be able to transfer it efficiently into the bottom 13 of the first distillation column and to be able to remove it from there.

In the reactor 1, a Mannich reaction takes place in the liquid phase, in which formaldehyde and propionaldehyde are converted to methacrolein in the presence of water and in the presence of the homogeneous catalyst.

The reaction temperature at the outlet of the reaction zone of reactor 1 is chosen such that it is preferably in the range from 100° C. to 210° C., more preferably in the range from 110° C. to 200° C., even more preferably in the range from 120° C. to 190° C. and very especially preferably in the range from 130° C. to 180° C. it is possible thereby to achieve a high conversion and a good yield.

The pressure in the reactor 1 is chosen at least at a sufficiently high level that the reaction mixture remains in liquid form in the reactor 1. With these provisions, an appropriate pressure is set in the reactor 1, which is preferably in the range from 15 to 100 bar, more preferably in the range from 18 to 80 bar, even more preferably in the range from 22 to 50 bar and very especially preferably in the range from 25 to 40 bar. The pressures are absolute pressures.

Even after the liquid reaction mixture has left the reaction zone of the reactor 1, the Mannich reaction and also other further reactions, for example conversion of methacrolein to dimethacrolein or methacrolein oligomerization, can still proceed to a considerable degree, especially when the reaction mixture is still under the pressure within the reaction zone, and essentially still has the temperature that it has on exiting from the reaction zone. The reaction residence time in the present context is understood to mean the average time that elapses between the entry of the reactants into the reaction zone of the reactor 1 and the commencement of expansion of the reaction mixture in the expansion valve 3. The dwell time in the reaction zone is preferably in the range from 0.001 minute to 25 minutes, more preferably in the range from 0.001 minute to 10 minutes, even more preferably in the range from 0.1 second to 300 seconds, very especially preferably in the range from 1 second to 50 seconds, even further preferably in the range from 5 to seconds. It is possible thereby to efficiently limit side reactions and further reactions with a good yield.

The reaction mixture contains methacrolein and the accompanying components water, unconverted formaldehyde, unconverted propionaldehyde and catalyst. It may also contain one or more of the following further accompanying components:
- methanol, if methanol was present in the fresh aqueous formaldehyde solution
- dimethacrolein
- trimethylamine, if dimethylamine is used as base
- high boilers, especially high-boiling aldolization products
- oligomers, especially oligomers of methacrolein
- stabilizer (e.g. Tempol)
- dimers of propionaldehyde The reaction mixture is routed to the expansion valve 3 by means of the reactor removal conduit arrangement 2 and, by means of the expansion valve 3, expanded to a desired pressure, for example to a pressure in the range from 500 mbar (absolute) to standard pressure. The pressure relief results in conversion of at least a portion of the reaction mixture from the liquid phase to the gaseous phase, which gives rise to a first expansion mixture, namely the fraction of the reaction mixture that is converted to the gas phase as a result of the expansion. The fraction of the reaction mixture remaining in the liquid phase after the expansion is a second expansion mixture.

Since the methacrolein-water azeotrope has a lower boiling point than water and is therefore more readily evaporated than water, the first expansion mixture contains a higher proportion of methacrolein than the second expansion mixture. It is quite possible here for more than 90% by weight of the methacrolein present in the reaction mixture overall to go into the first expansion mixture. In other words, the expanding by means of the expansion valve 3 is already a first step for purifying of methacrolein, even though the expansion valve 3 is not part of the methacrolein workup plant 110 according to the invention.

The reduction in pressure and the conversion of a portion of the reaction mixture to the gaseous phase lead to a reduction in the temperature of the portion of the reaction mixture converted to the gas phase (first expansion mixture) and of the portion of the reaction mixture remaining in the liquid phase (second expansion mixture). Consequently, no other cooling is required for this cooling effect.

The process is preferably conducted in such a way that the first and second expansion mixtures after the expansion have a temperature in the range from about 60 to 120° C., preferably a temperature in the range from about 70 to 110° C. and more preferably a temperature in the range from about 80 to 90° C. It has been found that, in these temperature ranges, the extent of the unwanted side reactions and further reactions that can take place is less than was thought. More particularly, the first and second expansion mixtures can remain within the temperature ranges specified for a few minutes, preferably for 0.1 to 15 minutes, more preferably 1 to 5 minutes, even further preferably 0.5 to 3 minutes. These are dwell times of good acceptability with regard to unwanted side reactions and further reactions.

The dwell time of the first expansion mixture in the expansion vessel 5 is preferably lower than that of the second expansion mixture.

If the reaction mixture supplied to the expansion valve 3 is, for example, at a temperature of 165° C. and a pressure of 35 bar (absolute) and the composition based on its total mass contains 63.51% by weight of water and 29.04% by weight of methacrolein, a rapid expansion to 0.85 bar (absolute) can lead to a temperature of the first and second expansion mixtures of 78.9° C. (cf. experimental example according to the invention).

The expansion valve removal conduit arrangement 4 routes the first expansion mixture and the second expansion mixture into the expansion vessel 5. In the expansion vessel 5, the first expansion mixture and the second expansion mixture are separated from one another.

The first expansion mixture is routed into the first condenser 9 via the first outlet 8 or the expansion vessel 5 and the first expansion vessel removal conduit arrangement 8. The second expansion mixture is routed into the first distillation column 11 via the second outlet 7 of the expansion vessel 5 and the second expansion vessel removal conduit arrangement 10.

Preferably, the expansion vessel 5 is operated in such a way that a good fill level of second expansion mixture is present therein, the dwell time of the second expansion mixture in the expansion vessel 5 being distinctly higher than the dwell time of the first expansion mixture.

The first expansion mixture is condensed in the first condenser 9.

In the first distillation column 11, the second expansion mixture is separated into a first distillation mixture and a second distillation mixture, the first distillation mixture being in the form of a gas phase at the top 12 of the first distillation column 11 and the second distillation mixture in the form of a liquid phase in the bottom 13 of the first distillation column 11. The first distillation mixture has a higher proportion by weight of methacrolein than the second distillation mixture. The first distillation mixture also contains unconverted propionaldehyde and unconverted formaldehyde. The second distillation mixture has a higher proportion by weight of water than the first distillation mixture. Moreover, the second distillation mixture contains at least the greater portion of the catalyst supplied by the second expansion mixture compared to the first distillation mixture. The second distillation mixture also contains unconverted formaldehyde.

It is possible to configure the process in the first distillation column 11 in such a way that virtually all the catalyst supplied by the second expansion mixture remains in the bottom 13 of the first distillation column 11.

The first distillation column 11 can be operated at standard pressure, for example, such that there is a temperature of somewhat above 100° C. in the bottom 13 thereof. The reason for the increase somewhat beyond 100° C. (standard pressure) is the catalyst content present in the bottom 13, as a result of which the boiling temperature of the second distillation mixture increases correspondingly. The temperature at the top 12 of the first distillation column 11 at standard pressure may be chosen within the range from 68 to 98° C., preferably within the range from 80 to 90° C. This means that more water gets into the top 12 than at lower temperatures at the top 12.

The first distillation mixture is routed into the first condenser 9 via the first distillation column removal conduit arrangement 14 and likewise condensed therein. The condensate from the second condenser 9 contains an organic phase (first separation mixture) containing methacrolein, and an aqueous phase (second separation mixture).

The condensate from the first condenser 9 is routed into the first phase separator 18 via the condensate outlet 16 thereof and the condenser removal conduit arrangement 17. The organic phase and aqueous phase, i.e. first and second separation mixtures, are separated from one another therein. The organic phase, i.e. the first separation mixture, is removed via the first outlet 19 of the first phase separator 18 and the first phase separator removal conduit arrangement 21, for example into a tank or a further processing plant, for example a plant for preparation of methyl methacrylate. The aqueous phase, i.e. the second separation mixture, is routed via the second outlet 20 of the first phase separator 18 and the second phase separator removal conduit arrangement 22 into the second distillation column 23. The proportion of water in the second separation mixture, based on the total mass of the second separation mixture, may quite possibly be 75% by weight or higher. The methacrolein content in the second separation mixture, based on the total mass of the second separation mixture, may quite possibly be in the range from 2% to 10% by weight. The methanol content in the second separation mixture, based on the total mass of the second separation mixture, may quite possibly be in the range from 1% to 10% by weight. The second separation mixture may also contain formaldehyde. It will be apparent that the totality of all constituents of the second separation mixture together makes up 100% by weight of the total mass of the second separation mixture.

By virtue of the second separation mixture being routed into the second distillation column 23 and not into the first distillation column 11, less water gets into the first distillation column 11. As a result, the concentration of the catalyst in the bottom 13 of the first distillation column 11 is higher than if the second separation mixture were to be introduced into the first distillation column 11. Since the amount of water returnable to the reactor 1 is limited, the amount of the second distillation mixture returnable to the reactor 1 is also limited owing to the amount of water present therein. Since the second distillation mixture according to the present invention contains a relatively high proportion of catalyst, a relatively large portion of this catalyst can be returned to the reactor 1. It is accordingly possible to save fresh catalyst.

Since the first distillation column 11 is supplied with less water, a small amount of second distillation mixture is also obtained. Thus, if second distillation mixture is to be disposed of, a smaller amount of second distillation mixture has to be disposed of.

The second separation mixture is separated in the second distillation column 23 into a third distillation mixture and a fourth distillation mixture, wherein the third distillation mixture is in the form of a gas phase at the top 24 of the second distillation column 23 and comprises methacrolein, and the fourth distillation mixture is in the form of a liquid phase at the bottom 25 of the second distillation column 23 and comprises water. Since the catalyst for the most part gets into the bottom 13 of the first distillation column 11, a correspondingly small amount of catalyst gets into the bottom of the second distillation column 23. Accordingly, the fourth distillation mixture is less problematic in terms of its environmental properties than the second distillation mixture. Since it is possible to operate the first distillation column 11 in such a way that almost all the catalyst present in the second expansion mixture collects in the bottom 13 of the first distillation column 11, and since it is also additionally possible, with good effectiveness, to prevent drops and droplets of second expansion mixture in the expansion vessel 5 from leaving it via the first outlet 6 thereof, it is possible to obtain a distillation mixture containing only a small amount of or barely any catalyst. It is thus possible to obtain a fourth distillation mixture which, with regard to the catalyst, causes little or barely any environmental pollution and can easily be disposed of in this regard, for example by releasing it into a communal water treatment plant.

The second distillation column 23 can be operated, for example, at standard pressure such that there is a temperature in the range from about 100 to 102° C. in its bottom 25, in order to promote passage of the low boilers, for example methanol and methacrolein, into the top 24 the second distillation column.

The temperature at the top 24 of the second distillation column at standard pressure may be chosen within the range from 65 to 99° C., preferably in the range from 70 to 95° C. This promotes good depletion of low boilers in the wastewater.

For example, it is possible to obtain a third distillation mixture which, based on its total mass, contains more than 30% by weight of methacrolein and more than 40% by weight of water. As a further component, it may contain methanol in particular.

It is possible here to obtain, for example, a fourth distillation mixture which, based on its total mass, contains more than 98% by weight of water and less than 1% by weight of methanol and has been very substantially freed of methacrolein.

The third distillation mixture is routed through the third distillation column removal conduit arrangement 26 from the top 24 of the second distillation column 23 into the first condenser 9 and condensed therein.

The fourth distillation mixture is discharged from the preparation plant via a fourth distillation column removal conduit arrangement 27 from the bottom 25 of the second distillation column 23. It can be collected in a tank or suppled to a further processing plant, for example a preparation plant for preparation of methyl methacrylate, wherein the methacrolein present in the fourth distillation mixture is a reactant for preparation of methyl methacrylate.

The second distillation mixture is routed via the first section of the second distillation column removal conduit arrangement 15. Subsequently,

- the portion of the second distillation mixture that is to be routed to the reactor 1 is routed into the second section 30 of the second distillation column removal conduit arrangement 15 and hence to the reactor 1,
- the portion of the second distillation mixture that is to be routed out of the methacrolein workup plant 110 is routed into the third section 31 of the second distillation column removal conduit arrangement 15, and
- the portion of the second distillation mixture that is to be routed into the membrane plant 28 is routed into the fourth section 32 of the second distillation column removal conduit arrangement 15.

If the third section 31 of the second distillation column removal conduit arrangement 15 leads not just out of the methacrolein workup plant 110 but also out of the preparation plant 100 overall, as is the case in the first embodiment of the invention, the portion of the second distillation mixture that is routed into the third section 31 of the second distillation column removal conduit arrangement 15 is the portion of the second distillation mixture that is to be discharged from the preparation plant 100 overall.

In the membrane plant 28, at least a portion of the catalyst present in the second distillation mixture is retained (retentate mixture). Accordingly, the retentate mixture has a higher concentration of catalyst than the second distillation mixture. The permeate mixture from the membrane plant 28 has a correspondingly lower proportion of catalyst. Accordingly, the permeate mixture, with regard to its catalyst content, is less environmentally polluting than the retentate mixture. With a correspondingly effective membrane plant, it is possible to obtain a permeate mixture having a sufficiently low catalyst concentration that the permeate mixture can be disposed of without any problem with regard to its catalyst concentration, for example by releasing it into a communal water treatment plant.

A preferred membrane plant is a reverse osmosis membrane plant.

The retentate mixture is routed via the first outlet 33 of the membrane plant 28 into the first section 36 of the first membrane plant removal conduit arrangement 35. The portion of the retentate mixture that is to be routed into the reactor 1 is routed through the second section 37 of the first membrane plant removal conduit arrangement 35 into the second section 30 of the second distillation column removal conduit arrangement 15. The portion of retentate mixture that is to be routed out of the preparation plant 100 is discharged from the preparation plant 100 through the third section 38 of the first membrane plant removal conduit arrangement 35.

Permeate mixture is removed from the preparation plant 100 via the second outlet 34 of the membrane plant 28 and the second membrane plant removal conduit arrangement 39.

If the permeate mixture contains a sufficiently small amount of catalyst, it can, at least with regard to its catalyst content, be released into the public water treatment plant for disposal.

If the aim is to dispose of catalyst, trimethylamine and/or unwanted high boilers present in the second distillation mixture, the disposal or retentate mixture is more favourable than the direct disposal of second distillation mixture via the third section 31 of the second distillation column removal conduit arrangement 15 in that the retentate mixture contains less water based on the same amount of catalyst, trimethylamine and/or unwanted high boilers. If the disposal is to be effected, for example, by addition to an incineration, less energy is required for the disposal of retentate mixture since less water has to be concomitantly evaporated than if the same amount of catalyst, triethylamine and/or unwanted high boilers were to be incinerated by adding second distillation mixture to the incineration.

The conversion of dimethylamine to triethylamine increases the dimethylamine content in the second distillation mixture at the expense of the dimethylamine content through the recycling or second distillation mixture and/or retentate mixture to the reactor 1. Too great a decrease in dimethylamine in favour of triethylamine correspondingly worsens the methacrolein yield in the reactor 1, or entails a corresponding increase in the reaction temperature in order to efficiently counter the drop in the methacrolein yield in the reactor 1. However, too high a reaction temperature promotes the formation of unwanted by-products. The amount of trimethylamine which is returned to the reactor 1 may especially be reduced by removing second distillation mixture via the third section 31 of the second distillation column removal conduit arrangement 15 and/or retentate mixture via the third section 38 of the first membrane plant removal conduit arrangement 35. Catalyst thus lost can be compensated for by the supplying of fresh catalyst to the reactor 1.

The amount of water that can be fed into the reactor 1 is limited. If the amount of water present in the second distillation mixture obtained is higher than the amount of water that can or should be recycled into the reactor 1, and therefore not al the second distillation mixture obtained can or should be recycled into the reactor 1, not all the catalyst present in the second distillation mixture can be reused. The amount of the catalyst present in the second distillation mixture obtained that can be returned to the reactor 1 can be increased by reducing the amount of the second distillation mixture returned to the reactor 1 and increasing the amount of the retentate mixture introduced into the reactor 1.

The mixture or mixtures introduced into the second section 30 of the second distillation column removal conduit arrangement 15 from the first section 29 of the second distillation column removal conduit arrangement 15 and/or the second section 37 of the membrane plant removal conduit arrangement 35 especially return unconverted formaldehyde, water and catalyst to the reactor 1.

The reactor 1 can be supplied with fresh catalyst by muting an appropriate amount of acid or acids and bases or bases from the acid source 46 and base source 44 into the reactor 1.

The formaldehyde and propionaldehyde reactants are fed to the reactor 1 from the formaldehyde source 30 and the propionaldehyde source 42.

Reference is made to FIG. 2. The inventive preparation plant 200 of the second embodiment of the invention, illustrated schematically in a flow diagram therein, differs only partially from the preparation plant 100 of the first embodiment of the invention. Solely differences are addressed hereinafter.

By contrast with the preparation plant 100 of the first embodiment of the invention, the preparation plant 200 of the second embodiment has a methacrolein workup plant 210 that additionally has a second condenser 51. A third distillation column removal conduit arrangement 50 is provided, which, by contrast with the third distillation column removal conduit arrangement 26 of the first embodiment or the invention, fluidically connects the top 24 of the second distillation column 23 not to the first condenser 9 but to the second condenser 51, it being possible to route third distillation mixture from the top 24 of the second distillation column 23 through the third distillation column removal conduit arrangement 50 of the second embodiment of the invention into the second condenser 51. The third distillation mixture can be condensed in the second condenser 51. The second condenser 51 has a condensate outlet 52 fluidically connected by a second condenser removal conduit arrangement 53 to the first phase separator 18, it being possible to route condensate from the second condenser 51 through the second condenser removal conduit arrangement 53 from the second condenser 51 into the first phase separator 18.

The second condenser 51 can condense the third distillation mixture independently of the first condenser 9. Since the second condenser 51 is fluidically connected to the first phase separator 18, the first phase separator 18 can also be utilized for further workup of the condensate from the second condenser 51. In other words, no second phase separator is needed.

Reference is made to FIG. 3. The preparation plant 300 of the third embodiment of the invention, illustrated schematically in a flow diagram therein, differs only partially from the preparation plant 200 of the second embodiment of the invention. Solely differences are elucidated hereinafter.

By contrast with the preparation plant 200 of the second embodiment of the invention shown in FIG. 2, the methacrolein workup plant 310 of the preparation plant 300 of the third embodiment of the invention additionally has a second phase separator 61 with which an organic phase (third separation mixture) present in the condensate of the second condenser 51 can be separated from an aqueous phase (fourth separation mixture) present in the condensate of the second condenser 51. A second condenser removal conduit arrangement 60 is provided here, which fluidically connects the condensate outlet 52 of the second condenser 51 to the second phase separator 61 rather than to the first phase separator 18, by means of which it is possible to route condensate from the second condenser 51 from the second condenser 51 through the second condenser removal conduit arrangement 60 into the second phase separator 61. The second phase separator 61 has a first outlet 62 for removal of the organic phase separated off, i.e. for removal of third separation mixture, and a second outlet 63 for removal of the aqueous phase, i.e. for removal of fourth separation mixture. The first outlet 62 of the second phase separator 61 is fluidically connected to the first phase separator removal conduit arrangement 21 by a third phase separator removal conduit arrangement 64, by means of which third separation mixture can be introduced through the third phase separator removal conduit arrangement 64 into the first phase separator removal conduit arrangement 21 and can be removed together with first separation mixture through the section of the first phase separator removal conduit arrangement 21 adjoining the discharge site on the downstream side.

Condensate from the second condenser 51 is routed into the second phase separator 61. Third and fourth separation mixture are separated therein, with the third separation mixture containing more methacrolein than the fourth separation mixture and the fourth separation mixture containing more water than the third separation mixture. The third separation mixture, just like the first separation mixture, has a good methacrolein content and can be used for further processing, for example for preparation of methylmethacrolein.

In the third embodiment of the invention, the third separation mixture is routed through the third phase separator removal conduit arrangement 64 and through the section of the first phase separator removal conduit arrangement 21 adjoining the discharge site on the downstream side. In other words, in the third embodiment of the invention, first and third separation mixture are combined.

The second outlet 63 of the second phase separator 61 is fluidically connected to the second distillation column 23 by a fourth phase separator removal conduit arrangement 65, it being possible to route fourth separation mixture through the fourth phase separator removal conduit arrangement 65 from the second phase separator 61 into the second distillation column 23. Through the introduction of fourth separation mixture into the second distillation column 23, it is possible to separate methacrolein present in the fourth separation mixture from water present in the fourth separation mixture.

Reference is made to FIG. 4. The fourth embodiment of the invention illustrated schematically in FIG. 4 differs only partially from the first embodiment of the invention shown in FIG. 1. Solely differences of the fourth embodiment of the invention from the first embodiment of the invention are elucidated hereinafter.

In the preparation plant 400 of the fourth embodiment of the invention, a third distillation column removal conduit arrangement 70 is provided, which fluidically connects the top 24 of the second distillation column 23 to the first distillation column 11 of the methacrolein workup plant 410 of the fourth embodiment of the invention rather than to the first condenser 9. It being possible to route third distillation mixture from the top 24 of the second distillation column 23 through the third distillation column removal conduit arrangement 70 into the first distillation column 11. Through the introduction of third distillation mixture into the first distillation column 11, the third distillation mixture is supplied to the appropriate further workup. The third distillation mixture does also contain water. However, the associated input of water into the first distillation column 11 is manageable and is much smaller than if second separation mixture were to be introduced into the first distillation column 11. The advantages that are achieved thereby, that the second separation mixture is introduced not into the first distillation column 11 but into the second distillation column 23, are maintained to a good degree.

Reference is made to FIG. 5. The fifth embodiment of the invention differs only partially from the fourth embodiment of the invention. Solely differences are addressed hereinafter.

In the preparation plant 500 of the fifth embodiment of the invention, by contrast with the preparation plant 400 of the fourth embodiment of the invention, a third distillation column removal conduit arrangement 80 is provided, which connects the top 24 of the third distillation column 23 to the expansion vessel 5 rather than to the first distillation column 11. This third distillation column removal conduit arrangement 80 can route third distillation mixture from the top 24 of the second distillation column 23 into the expansion vessel 5. Through the introduction of third distillation mixture into the expansion vessel 5, the third distillation mixture is supplied to the appropriate further workup. More particularly, the third distillation mixture, since it is gaseous, flows together with the first expansion mixture through the first expansion vessel removal conduit arrangement 8 into the first condenser 9 and is condensed therein. As part of the condensate of the first condenser 9, the condensed third distillation mixture is routed through the first condenser removal conduit arrangement 17 into the first phase separator 18 and passes through the separation process therein.

Reference is made to FIGS. 6 to 9. The preparation plants 600, 700, 800, 900 of the sixth, seventh, eighth and ninth embodiments shown therein have methacrolein workup plants 810, 710, 810 and 910 that do not have an expansion vessel 5 and consequently also do not have any first or second expansion vessel removal conduit arrangements 8, 10. In these embodiments, an expansion valve removal conduit arrangement 90 is provided, which fluidically connect the expansion valve 3 to the first distillation column 11. As a result, expanded reaction mixture can be routed into the first distillation column 11. Expansion is thus effected into the first distillation column 11. Otherwise, the preparation plant 600 of the sixth embodiment of the invention corresponds to the preparation plant 100 of the first embodiment of the invention, the preparation plant 700 of the seventh embodiment of the invention corresponds to the preparation plant 200 of the second embodiment of the invention, the preparation plant 800 of the eighth embodiment of the invention corresponds to the preparation plant 300 of the third embodiment of the invention and the preparation plant 900 of the ninth embodiment of the invention corresponds to the preparation plant 400 of the fourth embodiment of the invention.

In the sixth to ninth embodiments of the invention, the composition of the first distillation mixture is similar to the composition of the first distillation mixture of the first to fifth embodiments of the invention, and the composition of the second distillation mixture is similar to the composition of the second distillation mixture of the first to fifth embodiments of the invention.

Since no expansion vessel is provided in the sixth to ninth embodiments of the invention, a greater amount of gas flows through the first distillation columns of these embodiments of the invention. For adjustment of the first distillation columns thereto, these may, for example, be broader in the upward direction and/or additionally have a side draw for the gas phase.

Further possible variations that can be implemented individually or in any desired combinations are described hereinafter.

Preparation plants that combine multiple or all of the first, second, third, fourth and fifth embodiments with one another are possible, as are preparation plants that combine multiple or all of the sixth, seventh, eighth and ninth embodiments with one another.

Individual or all distillation columns may have a reboiler circuit through which respective bottoms mixture is routed and in which this is heated.

Individual or all condensation columns may have a condenser circuit separate from the respective methacrolein workup plant, with which tops mixture is condensed and fed back into the distillation column in question, wherein the separate condenser circuit has a dedicated condenser.

It is also possible to utilize the first condenser 9 as well for the condensing of the tops mixture from the first distillation column; in other words, no separate condenser would be required in this case. It is additionally possible to utilize the respective second condenser 51 as well for the condensing of the tops mixture from the second distillation columns of the second, third, seventh and/or eighth embodiments of the invention; in other words, in this case too, no separate condenser would be required.

Individual or all distillation columns may each have a droplet retaining unit with which drops and droplets can be prevented from leaving the distillation column in question via the top thereof. The droplet retaining unit may take the form, for example, of a fine-mesh sieve, of what is called a demister, or of a liquid release unit with which liquid is released within the distillation column in the direction of the bottom of the distillation column in question, where this liquid collects ascending drops and droplets, by means of which the liquid of the drops and droplets is then moved in the direction of the bottom. The droplet retention unit increases the separating efficiency of the distillation column in question.

The second distillation column 23 may be a packed column or a tray column or a mixed form thereof.

Individual or all distillation columns may contain random packings and/or structured packings.

One or more of the condensers 9, 51 may have a ventilation via which offgas from one or more reactions can be removed.

One or more of the condensers 9, 51 may be in multistage form, for example in two-stage form. In the two-stage case, it would be possible with the first condenser stage, for example, to achieve cooling to about 30 to 40° C., and with the second condenser stage, for example, cooling to about 3 to 10° C., preferably to 4° C. Multistage operation saves cooling brine.

If multistage condensers are used, it is possible to recycle a portion of the condensate into the first condensation stage and add a stabilizer that acts against polymerization.

One or more of the condensers 9, 51 may have a gas phase removal unit with which any gas phase present in the condenser in question can be removed from this condenser.

Second separation mixture can be admixed with an agent that counteracts polymerization, for example the polymerization of methacrolein and/or of dimethylamine. This modified second separation mixture can be introduced into one or more condensers in order to counteract polymerization even therein.

The substances introduced into the reactor 1 may be preheated, for example, to a temperature of about 130° C.

The reactor 1 may take the form of a tubular reactor.

The base or bases introduced into the reactor 1 from the base source 44, acid or acids from the acid source 48 and/or the recycle stream which is introduced into the reactor 1 through the second section 30 of the second distillation column removal conduit arrangement 15 coming from the first section 29 of the second distillation column removal conduit arrangement 15 and/or the second section 37 of the first membrane plant removal conduit arrangement 35 can be more significantly preheated than the fresh formaldehyde and the fresh propionaldehyde that are introduced into the reactor 1 from the formaldehyde source 40 and the propionaldehyde source 42. It is possible here to heat the acid or acids, the base or bases and/or the recycle stream mentioned that such a degree that a desired premixing temperature is attained only after mixing thereof with the fresh formaldehyde and the fresh propionaldehyde. In this way, the fresh formaldehyde and the fresh propionaldehyde remain for longer at a temperature lower than the desired premixing temperature. The recycled material mentioned can also be preheated.

Heat can be removed from the second distillation mixture removed from the bottom 13 of the first distillation column 11, and can be utilized at least partly for preheating of at least a portion of the substances introduced into the reactor 1.

Individual or all expansion vessels 5—if present—may have a droplet retaining unit with which drops and droplets of second expansion mixture can be prevented from leaving the expansion vessel 5 via the first outlet 6 thereof together with first expansion mixture. The droplet retaining unit may take the form, for example, of a fine-mesh sieve. The droplet retaining unit increases the separation efficiency of the expansion vessel 5. Accordingly, the amount of catalyst that leaves the expansion vessel 5 via the first 6 thereof is also reduced.

The droplet retaining unit of the expansion vessel 5 may take the form of a "demister".

The expansion vessel 5 may have a spraying unit with which the droplet retention device can be sprayed from beneath with a liquid in order to increase the effect of the droplet retaining unit. The liquid may, for example, be second expansion mixture or a liquid containing an agent that counteracts the polymerization of methacrolein and/or dimethylamine.

If required, for example, stabilizer can be added to the first condenser 9 and/or the second section of the second distillation column removal conduit arrangement 15.

In the first to fifth embodiments of the invention, the expansion valve 3, as shown in FIGS. 1 to 5, is disposed outside the expansion vessel 5. However, it is also possible to dispose the expansion valve 3 within the expansion vessel 5 or to integrate it into the wall thereof. In such cases, there are also possible configurations in which it is possible to dispense with an expansion valve removal conduit arrangement.

In the sixth to ninth embodiments of the invention, the expansion valve 3, as shown in FIGS. 6 to 9, is disposed upstream of the first distillation column 11. However, it is also possible to provide it integrated within the first distillation column 11 or into the wall of the first distillation column 11. There are also possible variants here in which it is possible to dispense with an expansion valve removal conduit arrangement.

In the first to fifth embodiments of the invention, the first expansion vessel removal conduit arrangement 8 and the first distillation column removal conduit arrangement 14 lead separately into the first condenser 9. However, it is also possible that the first expansion vessel removal conduit arrangement 8 and the first distillation column removal conduit arrangement 14 are combined and are connected to a common inlet of the first condenser 9 in combined form, i.e. fluidically connected to this common inlet.

In the first and sixth embodiments of the invention, the third distillation column removal conduit arrangement 26 leads separately into the first condenser. However, it is also possible that the third distillation column removal conduit arrangement 28 and the first distillation column removal conduit arrangement 14 are combined and are connected to a common inlet of the first condenser 9 in combined form, i.e. fluidically connected to this common inlet.

In the first to ninth embodiments of the invention, a second distillation column removal conduit arrangement 15 is provided. However, it is also possible to provide two separate second distillation column removal conduit arrangements, wherein one has the first and second and optionally third sections 29, 30, 31 of the second distillation column removal conduit arrangements 15 of the first to ninth embodiments of the invention and consequently fluidically connects the bottom 13 of the first distillation column 11 especially to the reactor 1, and the other fluidically connects the bottom 13 of the first distillation column 11 to the membrane plant 28.

In the second, third, seventh and eighth embodiments of the invention, the third distillation column removal conduit arrangement 50 connects the top 24 of the second distillation column 23 to the second condenser 51 only. It is also possible to provide a third distillation column removal conduit arrangement that fluidically connects the top 24 of the second distillation column 23 both to the first condenser 9 and to the second condenser 51.

In the third and eighth embodiments of the invention, first and third separation mixtures are combined. However, it is also possible to provide the third phase separator removal conduit arrangement in such a way that it is not fluidically connected to the first phase separator removal conduit arrangement 21 but is fluidically connected to a tank for a further processing plant separately therefrom.

The membrane plant 28 is always optional and can be omitted.

The membrane plant 28 may be in one-stage or multistage form.

The membrane plant is preferably a three-stage reverse osmosis membrane plant, the first stage of which is operated within a pressure range from 80 to 120 bar (absolute), the second stage of which is operated within a pressure range from 20 to 80 bar (absolute), and the third stage of which is operated within a pressure range from 20 to 40 bar (absolute). When the base used is dimethylamine and the acid used is acetic acid. It is possible with a reverse osmosis membrane plant thus operated to retain more than 99% of the dimethylamine present in the distillation mixture, about 80% of acetic acid present in the second distillation mixture, and about 70% to 80% of the formaldehyde present in the second distillation mixture.

The membrane plant 28 may be provided with a cooling apparatus with which the working temperature in particular of the membrane plant can be regulated.

In the first to ninth embodiments of the invention, the formaldehyde feed arrangement 41, the propionaldehyde feed arrangement 43, the base feed arrangement 45 and the acid feed arrangement 47 are fluidically connected to the second section 30 of the second distillation column removal conduit arrangement 15. Alternatively, it is possible to fluidically connect the formaldehyde reed arrangement 41, the propionaldehyde reed arrangement 43, the base feed arrangement 45 and/or the acid feed arrangement 47 directly to the reactor 1, by means of which formaldehyde, propionaldehyde, base(s) and/or acid(s) can be introduced directly into the reactor 1.

In the first to ninth embodiments of the invention, fresh formaldehyde, fresh propionaldehyde, fresh acid or acids and fresh base or bases are supplied from separate sources. It is also possible to premix fresh formaldehyde and fresh propionaldehyde or supply a mixture with formaldehyde and propionaldehyde from an appropriate source and/or premix fresh acid or acids and fresh base or bases or a mixture with acid or acids and base or bases from an appropriate source.

If there is no premixing of acid or acids and bases or bases, it is thus possible to route acid or acids into the second section 30 of the second distillation column removal conduit arrangement 15, before base or bases are routed into the second section 30 of the second distillation column removal conduit arrangement 15. With this sequence, it is more easily possible to counteract a local excess of base.

Inventive Experimental Example

The Aspen Plus V8.8 simulation program from Aspen Technologies, Inc. was used to simulate the inventive operation of a preparation plant of the invention, apart from the variations enumerated hereinafter according to the first embodiment of the invention, but using the reference numerals of the first embodiment of the invention hereinafter in spite of these variations:

The preparation plant does not have a membrane plant.

The formaldehyde feed arrangement and the propionaldehyde feed arrangement are combined to form a formaldehyde-propionaldehyde feed arrangement that opens into the second section of the second distillation column removal conduit arrangement 15.

The first condenser 9 has a gas phase removal unit fluidically connected to an incineration plant for incineration of the gas phase.

The first condenser 9 has a droplet retaining unit arranged upstream of its first outlet 6, in the form of a "demister".

The first condenser 9 has a collective inlet that combines the feed streams of first expansion mixture, first distillation mixture and third distillation mixture.

The first condenser 9 is in two-stage form.

From the bottom 13 of the first distillation column 11, recycle stream flows through the second section 30 of the second distillation column removal conduit arrangement 15 in the direction of the reactor 1. From the acid source 44, aqueous acetic acid solution is introduced via the acid feed arrangement 45 into the second section 30 of the second distillation column removal conduit arrangement 15. From the base source 46, aqueous dimethylamine solution is introduced via the base feed arrangement 47 into the second section 30 of the second distillation column removal conduit arrangement 15. The resultant mixture is preheated to 130° C.

Coming from the formaldehyde source 40, aqueous formaldehyde solution is introduced via the formaldehyde feed arrangement 41 into the formaldehyde-propionaldehyde feed arrangement and, from the propionaldehyde source 42, aqueous propionaldehyde solution is introduced via the propionaldehyde feed arrangement 43 into the formaldehyde-propionaldehyde feed arrangement. The resultant mixture of formaldehyde and propionaldehyde solution is preheated to 130° C. and introduced into the second section 30 of the second distillation column removal conduit arrangement 15.

The mixture now present in the second section 30 of the second distillation column removal conduit arrangement 15 is introduced into the reactor 1 which, in this inventive experimental example, takes the form of a tubular reactor.

The dwell time in reactor 1 is 9.5 s, and the pressure in the reactor is 35 bar (absolute). Virtually full conversion is achieved. The reaction mixture leaving the reactor has a temperature of 165° C. In the expansion vessel 5, the reaction mixture is expanded to 0.85 bar (absolute).

The first stage of the first condenser 9 is cooled with cooling water, and the second stage with cooing brine at a temperature of 4° C.

The gas phase present in the first condenser is sent to incineration via a gas phase removal unit.

Table 1 below reports the mass flow rate, the pressure, temperature and the composition of some streams in the inventive experimental example. In Table 1, "Stream A" means: dimethylamine solution stream through the base feed arrangement 47, "Stream B" means: acetic acid solution stream through the acid feed arrangement 45, "Stream C" means: propionaldehyde solution stream through the propionaldehyde feed arrangement 43, "Stream D" means: formaldehyde solution stream through the formaldehyde feed arrangement 41, "Stream E" means: stream entering reactor 1, "Stream F" means: reaction mixture stream through the reactor removal conduit arrangement 2, "Stream G" means: stream of first expansion mixture through the first expansion vessel removal conduit arrangement 8, "Stream H" means: stream of second expansion mixture through the second expansion vessel removal conduit arrangement 10, "Stream I" means: stream of first distillation mixture through the first distillation column removal conduit arrangement 14, "Stream J" means: stream of second distillation mixture through the first section 29 of the second distillation column removal conduit arrangement 15, "Stream K" means: stream of second distillation mixture which flows from the first section 29 of the second distillation column removal conduit arrangement 15 into the second section 30 of the second distillation column removal conduit arrangement 15, "Stream L" means: stream of second distillation mixture which flows from the first section 29 of the second distillation column removal conduit arrangement 15 into the third section 31 of the second distillation column removal conduit arrangement 15 and is sent to a disposal, "Stream M" means: stream through the collective inlet of the first condenser 9, "Stream N" means: stream of first separation mixture through the first phase separator removal conduit arrangement 21, "Stream O" means: stream or second separation mixture through the second phase separator removal conduit arrangement 22, "Stream P" means: stream or third distillation mixture through the third distillation column removal conduit arrangement 28, "Stream Q" means: stream of fourth distillation mixture through the fourth distillation column removal conduit arrangement 27, the unit "%" represents % by weight based on the total mass of the stream in question and the number of decimal places represents the accuracy of the numerical values.

TABLE 1

| | Conditions | | | Composition | | | |
|---|---|---|---|---|---|---|---|
| | Mass flow rate in kg/h | Temperature in ° C. | Pressure in bar (absolute) | Formaldehyde | Water | Methanol | Dimethacrolein |
| Stream A | 361 | 30.0 | 1.01 | 0.00% | 60.00% | 0.00% | 0.00% |
| Stream B | 264 | 30.0 | 1.01 | 0.00% | 20.00% | 0.00% | 0.00% |

TABLE 1-continued

| Stream | | | | | | | |
|---|---|---|---|---|---|---|---|
| Stream C | 11159 | 30.0 | 1.01 | 0.00% | 2.50% | 0.00% | 0.00% |
| Stream D | 10388 | 65.0 | 1.01 | 55.00% | 44.50% | 0.50% | 0.00% |
| Stream E | 44321 | 130.0 | 36.00 | 13.43% | 56.00% | 0.21% | 0.01% |
| Stream F | 44321 | 165.0 | 35.00 | 0.72% | 63.51% | 0.23% | 0.19% |
| Stream G | 16136 | 78.9 | 0.85 | 0.12% | 21.79% | 0.32% | 0.46% |
| Stream H | 28184 | 78.9 | 0.85 | 1.06% | 87.40% | 0.18% | 0.03% |
| Stream I | 573 | 78.4 | 0.80 | 0.13% | 23.29% | 0.34% | 0.48% |
| Stream J | 27614 | 94.7 | 0.83 | 1.08% | 88.72% | 0.18% | 0.02% |
| Stream K | 22148 | 94.7 | 0.83 | 1.08% | 88.72% | 0.18% | 0.02% |
| Stream L | 5466 | 94.7 | 0.83 | 1.08% | 88.72% | 0.18% | 0.02% |
| Stream M | 17442 | 79.5 | 0.80 | 0.12% | 22.89% | 0.93% | 0.45% |
| Stream N | 13242 | 20.0 | 0.72 | 0.07% | 1.65% | 0.38% | 0.58% |
| Stream O | 4199 | 20.0 | 0.72 | 0.28% | 90.34% | 2.69% | 0.01% |
| Stream P | 732 | 91.4 | 1.00 | 0.12% | 46.89% | 14.98% | 0.06% |
| Stream Q | 3467 | 99.6 | 1.00 | 0.31% | 99.52% | 0.09% | 0.00% |

| | Composition | | | | | |
|---|---|---|---|---|---|---|
| | Propionaldehyde | Methacrolein | Acetic acid | Dimethylamine | Remainder | Trimethylamine |
| Stream A | 0.00% | 0.00% | 0.00% | 40.00% | 0.00% | 0.00% |
| Stream B | 0.00% | 0.00% | 80.00% | 0.00% | 0.00% | 0.00% |
| Stream C | 97.30% | 0.00% | 0.00% | 0.00% | 0.20% | 0.00% |
| Stream D | 0.00% | 0.00% | 0.00% | 0.00% | 0.00% | 0.00% |
| Stream E | 24.50% | 0.01% | 2.36% | 1.52% | 1.80% | 0.16% |
| Stream F | 0.02% | 29.04% | 2.36% | 1.49% | 2.25% | 0.20% |
| Stream G | 0.04% | 77.06% | 0.03% | 0.00% | 0.17% | 0.00% |
| Stream H | 0.00% | 1.54% | 3.69% | 2.34% | 3.43% | 0.32% |
| Stream I | 0.04% | 75.10% | 0.03% | 0.00% | 0.60% | 0.00% |
| Stream J | 0.00% | 0.02% | 3.77% | 2.39% | 3.49% | 0.32% |
| Stream K | 0.00% | 0.02% | 3.77% | 2.39% | 3.49% | 0.32% |
| Stream L | 0.00% | 0.02% | 3.77% | 2.39% | 3.49% | 0.32% |
| Stream M | 0.04% | 75.35% | 0.03% | 0.00% | 0.19% | 0.00% |
| Stream N | 0.05% | 97.13% | 0.03% | 0.00% | 0.12% | 0.00% |
| Stream O | 0.00% | 6.58% | 0.04% | 0.00% | 0.06% | 0.00% |
| Stream P | 0.02% | 37.72% | 0.04% | 0.00% | 0.17% | 0.00% |
| Stream Q | 0.00% | 0.00% | 0.04% | 0.00% | 0.04% | 0.00% |

Noninventive Comparative Experimental Example

The Aspen Plus V8.8 simulation program from Aspen Technologies, Inc. was also used to simulate, as a noninventive comparative experiment example, the operation of a preparation plant not according to the invention. By contrast with the inventive experimental example, the preparation plant of the noninventive comparator experimental example does not have a second distillation column, and the second phase separator removal conduit arrangement is not fluidically connected to the first distillation column. The preparation process of the comparative experimental example not according to the invention accordingly varies from the preparation process or the inventive experimental example. In spite of these modifications, the reference numerals of the first embodiment of the invention are used hereinafter.

Table 2 below reports the mass flow rate, the pressure, temperature and the composition of some streams in the noninventive comparative experimental example. In Table 2, "Stream A" means: dimethylamine solution stream through the base feed arrangement 47, "Stream B" means: acetic acid solution stream through the acid feed arrangement 45, "Stream C" means: propionaldehyde solution stream through the propionaldehyde feed arrangement 43, "Stream D" means: formaldehyde solution stream through the formaldehyde feed arrangement 41, "Stream E" means: stream entering reactor 1.

"Stream F" means: reaction mixture stream through the reactor removal conduit arrangement 2, "Stream G" means: stream or first expansion mixture through the first expansion vessel removal conduit arrangement 8, "Stream H" means: stream of second expansion mixture through the second expansion vessel removal conduit arrangement 10, "Stream I" means: stream of first distillation mixture through the first distillation column removal conduit arrangement 14, "Stream J" means: stream of second distillation mixture through the first section 29 of the second distillation column removal conduit arrangement 15.

"Stream K" means: stream of second distillation mixture which flows from the first section 29 of the second distillation column removal conduit arrangement 15 into the second section 30 of the second distillation column removal conduit arrangement 15, "Stream L" means: stream of second distillation mixture which flows from the first section 29 of the second distillation column removal conduit arrangement 15 into the third section 31 of the second distillation column removal conduit arrangement 15 and is sent to a disposal, "Stream M" means: stream through the collective inlet of the first condenser 9, "Stream N" means: stream of first separation mixture through the first phase separator removal conduit arrangement 21, "Stream O" means: stream of second separation mixture through the second phase separator removal conduit arrangement 22, the unit "%" represents % by weight based on the total mass of the stream in question and the number of decimal places represents the accuracy of the numerical values.

TABLE 2

| | Conditions | | | Composition | | | |
|---|---|---|---|---|---|---|---|
| | Mass flow rate in kg/h | Temperature in °C. | Pressure in bar (absolute) | Formaldehyde | Water | Methanol | Dimethacrolein |
| Stream A | 544 | 30.0 | 1.01 | 0.00% | 60.00% | 0.00% | 0.00% |
| Stream B | 398 | 30.0 | 1.01 | 0.00% | 20.00% | 0.00% | 0.00% |
| Stream C | 11159 | 30.0 | 1.01 | 0.00% | 2.50% | 0.00% | 0.00% |
| Stream D | 10388 | 65.0 | 1.01 | 55.00% | 44.50% | 0.50% | 0.00% |
| Stream E | 43232 | 130.0 | 36.00 | 13.55% | 56.00% | 0.26% | 0.00% |
| Stream F | 43232 | 165.0 | 35.00 | 0.52% | 63.70% | 0.29% | 0.18% |
| Stream G | 16044 | 78.5 | 0.85 | 0.08% | 21.26% | 0.39% | 0.44% |
| Stream H | 27188 | 78.5 | 0.85 | 0.77% | 88.74% | 0.23% | 0.03% |
| Stream I | 1168 | 79.0 | 0.80 | 1.56% | 35.33% | 4.37% | 0.71% |
| Stream J | 30002 | 94.7 | 0.83 | 0.70% | 91.13% | 0.29% | 0.00% |
| Stream K | 20742 | 94.7 | 0.83 | 0.70% | 91.13% | 0.29% | 0.00% |
| Stream L | 9260 | 94.7 | 0.83 | 0.70% | 91.13% | 0.29% | 0.00% |
| Stream M | 17319 | 77.1 | 0.80 | 0.19% | 22.64% | 0.67% | 0.46% |
| Stream N | 13232 | 20.0 | 0.72 | 0.11% | 1.63% | 0.27% | 0.59% |
| Stream O | 4087 | 20.0 | 0.72 | 0.43% | 91.13% | 1.95% | 0.01% |

| | Composition | | | | | |
|---|---|---|---|---|---|---|
| | Propionaldehyde | Methacrolein | Acetic acid | Dimethylamine | Remainder | Trimethylamine |
| Stream A | 0.00% | 0.00% | 0.00% | 40.00% | 0.00% | 0.00% |
| Stream B | 0.00% | 0.00% | 80.00% | 0.00% | 0.00% | 0.00% |
| Stream C | 97.30% | 0.00% | 0.00% | 0.00% | 0.20% | 0.00% |
| Stream D | 0.00% | 0.00% | 0.00% | 0.00% | 0.00% | 0.00% |
| Stream E | 25.12% | 0.00% | 2.37% | 1.56% | 1.06% | 0.09% |
| Stream F | 0.02% | 29.76% | 2.36% | 1.53% | 1.52% | 0.13% |
| Stream G | 0.04% | 77.59% | 0.03% | 0.00% | 0.16% | 0.00% |
| Stream H | 0.00% | 1.54% | 3.74% | 2.43% | 2.32% | 0.21% |
| Stream I | 0.04% | 57.50% | 0.02% | 0.00% | 0.47% | 0.00% |
| Stream J | 0.00% | 0.00% | 3.39% | 2.20% | 2.10% | 0.19% |
| Stream K | 0.00% | 0.00% | 3.40% | 2.20% | 2.09% | 0.19% |
| Stream L | 0.00% | 0.00% | 3.40% | 2.20% | 2.09% | 0.19% |
| Stream M | 0.04% | 75.80% | 0.03% | 0.00% | 0.18% | 0.00% |
| Stream N | 0.05% | 97.21% | 0.03% | 0.00% | 0.10% | 0.00% |
| Stream O | 0.00% | 6.39% | 0.04% | 0.00% | 0.05% | 0.00% |

Comparison of Inventive Experimental Example and Noninventive Comparative Experimental Example If the inventive experimental example is compared with the noninventive comparative experimental example, it becomes clear that the stream of second distillation mixture through the first section 29 of the second distillation column removal conduit arrangement 15 (Stream J) in the inventive experimental example has a smaller proportion by mass, which derives especially from a lower absolute amount of water, and the concentration of dimethylamine and acetic acid is higher. In the inventive experimental example, it is thus possible to return more catalyst relative to the absolute amount of water to the reactor. If second distillation mixture is to be disposed of by sending it to incineration, the energy expenditure in the inventive experimental example relative to the absolute amount of dimethylamine or absolute amount of acetic acid is smaller since a smaller absolute amount of water has to be evaporated relative to the absolute amount of dimethylamine or the absolute amount of acetic acid.

If the dimethylamine solution stream through the respective base feed arrangement 47 (Stream A) and the acetic acid solution stream through the respective acid feed arrangement 45 (Stream B) are compared, it becomes clear that, in the inventive experimental example, much less dimethylamine and much less acetic acid was used relative to the absolute amount present in the stream of first separation mixture through the first phase separator removal conduit arrangement 21 (Stream N).

The invention claimed is:

1. A process for preparing methacrolein from formaldehyde and propionaldehyde in the presence of water and in the presence of a homogeneous catalyst based at least on an acid and a base, the process comprising:

S1: introducing formaldehyde, propionaldehyde, water, and the homogeneous catalyst based at least on the acid and the base into a reactor, S2: producing, in a liquid phase, a liquid reaction mixture in the reactor, wherein the reaction mixture comprises methacrolein and accompanying components, wherein the accompanying components comprise water, the catalyst, unconverted formaldehyde, and unconverted propionaldehyde, S3: introducing the reaction mixture into a methacrolein workup plant and at least partly separating off the accompanying components present in the reaction mixture in the methacrolein workup plant, wherein the at least partly separating off comprises:

S3.i: introducing at least a fraction of the reaction mixture into a first distillation column that forms part of the methacrolein workup plant and separating the at least a fraction of the reaction mixture at least into a first distillation mixture and a second distillation mixture, wherein the first distillation mixture is in a form of a gas phase at the top of the first distillation column and comprises methacrolein, and the second distillation mixture is in a form of a liquid phase at the bottom of the first distillation column and comprises water and the catalyst, S3.ii: introducing the first distillation mixture removed from the top of the first distillation column into a first condenser that forms part of the methacrolein workup plant and condensing the first distillation mixture, S3.iii: removing condensate from the first condenser, introducing the condensate into a first phase separator that forms part of the methacrolein workup plant and separating the condensate into a first separation mixture and a second separation mixture in the first phase separator, wherein the first separation mixture is in a form of an organic phase comprising methacrolein, and the second separation mixture is in a form of an aqueous phase, and S3.iv: removing the second distillation mixture from the bottom of the first distillation column, S4: introducing at least a portion of the second distillation mixture removed in S3.iv into the reactor, S5: introducing the second separation mixture into a second distillation column and separating the second separation mixture introduced at least into a third distillation mixture and a fourth distillation mixture, wherein the third distillation mixture is in a form of a gas phase at the top of the second distillation column and comprises methacrolein, and the fourth distillation mixture is in a form of a liquid phase at the bottom of the second distillation column and comprises water, S6: removing the third distillation mixture from the top of the second distillation column and introducing the third distillation mixture into the methacrolein workup plant, and S7: removing the fourth distillation mixture from the bottom of the second distillation column, wherein a pressure in the reactor is higher than in the first distillation column.

2. The process according to claim 1, wherein in S6, at least a portion of the third distillation mixture is introduced into the first condenser.

3. The process according to claim 1, wherein in SC, at least a portion of the third distillation mixture is introduced into and condensed in a second condenser that forms part of the methacrolein workup plant, and condensate is removed from the second condenser and introduced into the first phase separator.

4. The process according to claim 1, wherein in S6, at least a portion of the third distillation mixture is introduced into and condensed in a second condenser that forms part of the methacrolein workup plant, condensate is removed from the second condenser and introduced into a second phase separator that forms part of the methacrolein workup plant and is separated in the second phase separator into a third separation mixture and a fourth separation mixture, wherein the third separation mixture is in a form of an organic phase comprising methacrolein, and the fourth separation mixture is in a form of an aqueous phase.

5. The process according to claim 1, wherein in S6, at least a portion of the third distillation mixture is introduced into the first distillation column.

6. The process according to claim 1, wherein
the reaction mixture is expanded, which gives rise to a first expansion mixture which is a fraction of the reaction mixture that goes into a gas phase as a result of the expansion, and a second expansion mixture which is a fraction of the reaction mixture that remains in a liquid phase, the first expansion mixture and the second expansion mixture are separated in an expansion vessel that forms part of the methacrolein workup plant, the first expansion mixture is introduced into the first condenser and the second expansion mixture is introduced into the first distillation column.

7. The process according to claim 6, wherein in S6, at least a portion of the third distillation mixture is introduced into the expansion vessel.

8. The process according to claim 1, wherein at least a portion of the second distillation mixture removed in S3.iv is introduced into a membrane plant, at least a portion of catalyst present in the second distillation mixture introduced is retained in the membrane plant, and a retentate mixture comprising retained catalyst and a permeate mixture are removed from the membrane plant.

9. A preparation plant for preparation of methacrolein from formaldehyde and propionaldehyde in the presence of water and in the presence of a homogeneous catalyst based at least on an acid and a base according to the process according to claim 1, wherein the preparation plant comprises:

a reactor in which a reaction is performed in a liquid phase, in which methacrolein is formed from formaldehyde and propionaldehyde in the presence of water and in the presence of the homogeneous catalyst based at least on the acid and the base, a methacrolein workup plant for reducing a proportion accounted for by accompanying components in a reaction mixture or in a fraction of the reaction mixture, wherein the accompanying components comprise water, catalyst, unconverted formaldehyde, and unconverted propionaldehyde, and wherein the methacrolein workup plant comprises:

a first distillation column which has a top and a bottom, wherein the reaction mixture supplied or the fraction of the reaction mixture supplied is separated at least into a first distillation mixture in a form of a gas phase, containing methacrolein, and a second distillation mixture in a form of a liquid phase, containing water and the catalyst, a first condenser which has a condensate outlet, wherein the first distillation mixture is condensed, a first phase separator wherein a first separation mixture of an organic phase present in a condensate supplied by the first condenser is separated from a second separation mixture of an aqueous phase present in the condensate supplied by the first condenser, wherein the first phase separator has a first outlet for removing the first separation mixture and a second outlet for removing the second separation mixture, a first phase separator removal conduit arrangement which is fluidically connected to the first outlet from the first phase separator and through which the first separation mixture is removed from the first phase separator, a second phase separator removal conduit arrangement which is fluidically connected to the second outlet from the first phase separator and through which the second separation mixture is removed from the first phase separator, a first distillation column removal conduit arrangement which fluidically connects the top of the first distillation column and the first condenser and through which the first distillation mixture is routed from the first distillation column into the first condenser, a second distillation column removal conduit arrangement which fluidically connects the bottom of the first distillation column and the reactor and through which the second distillation mixture is routed out of the first distillation column into the reactor, and a condenser removal conduit arrangement which fluidically connects the condensate outlet of the first condenser and the first phase separator and through which the condensate from the first condenser is routed from the first condenser into the first phase separator, a second distillation column which has a top and a bottom, wherein the second separation mixture is separated at least into a methacrolein-containing third distillation mixture in a form of a gas phase and a water-containing fourth distillation mixture in a form of a liquid phase, wherein the second phase separator removal conduit arrangement fluidically connects the second outlet of the first phase separator to the second distillation column, and the second separation mixture is routed through the second phase separator removal conduit arrangement from the second outlet of the first phase separator into the second distillation column, a third distillation column removal conduit arrangement which is fluidically connected to the top of the second distillation column and by which the top of the second distillation column is fluidically connected to the methacrolein workup plant, wherein the third distillation mixture is routed through the third distillation column removal conduit arrangement from the top of the second distillation column into the methacrolein workup plant, and a fourth distillation column removal conduit arrangement which is fluidically connected to the bottom of the second distillation column and through which the fourth distillation mixture is removed from the second distillation column.

10. The preparation plant according to claim 9, wherein the third distillation column removal conduit arrangement fluidically connects the top of the second distillation column to the first condenser, and the third distillation mixture is routed through the third distillation column removal conduit arrangement from the top of the second distillation column into the first condenser.

11. The preparation plant according to claim 9, wherein the preparation plant has a second condenser that forms part of the methacrolein workup plant, the third distillation column removal conduit arrangement fluidically connects the top of the second distillation column to the second condenser, wherein the third distillation mixture is routed through the third distillation column removal conduit arrangement from the top of the second distillation column into the second condenser and is condensed in the second condenser, and the second condenser is fluidically connected to the first phase separator, wherein condensate from the second condenser is routed from the second condenser further into the first phase separator.

12. The preparation plant according to claim 9, wherein the preparation plant has a second condenser that forms part of the methacrolein workup plant, the third distillation column removal conduit arrangement fluidically connects the top of the second distillation column to the second condenser, wherein the third distillation mixture is routed through the third distillation column removal conduit arrangement from the top of the second distillation column into the second condenser and is condensed in the second condenser, and the second condenser is fluidically connected to a second phase separator that forms part of the methacrolein workup plant, wherein condensate from the second condenser is routed from the second condenser further into the second phase separator, —wherein a third separation mixture of an organic phase present n the condensate supplied by the first condenser is separated from a fourth separation mixture of an aqueous phase present in the condensate supplied by the second condenser, wherein the second phase separator has a first outlet for removal of the third separation mixture and a second outlet for removal of the fourth separation mixture.

13. The preparation plant according to claim 9, wherein the third distillation column removal conduit arrangement fluidically connects the top of the second distillation column to the first distillation column, and the third distillation mixture is routed through the third distillation column removal conduit arrangement from the top of the second distillation column into the first distillation column.

14. The preparation plant according to claim 9, wherein the methacrolein workup plant includes an expansion vessel wherein a first expansion mixture which is a fraction of the reaction mixture that goes into a gas phase as a result of expansion of the reaction mixture, and a second expansion mixture which is a fraction of the reaction mixture remaining in a liquid phase after the expansion of the reaction mixture, is separated from one another, and wherein the expansion vessel has a first outlet for removal of the first expansion mixture which is fluidically connected to the first condenser, wherein the first expansion mixture is routed into the first condenser, and a second outlet for removal of the second expansion mixture which is fluidically connected to the first distillation column, wherein the second expansion mixture is routed into the first distillation column.

15. The preparation plant according to claim 14, wherein the third distillation column removal conduit arrangement fluidically connects the top of the second distillation column to the expansion vessel, and the third distillation mixture is routed through the third distillation column removal conduit arrangement from the top of the second distillation column into the expansion vessel.

16. The preparation plant according to claim 9, wherein the bottom of the first distillation column is fluidically connected to the reactor, wherein the second distillation mixture is routed into the reactor.

17. The preparation plant according to claim 9, wherein the preparation plant has a membrane plant which is fluidically connected to the bottom of the first distillation column, and wherein at least a portion of catalyst present in the second distillation mixture fed to the membrane plant is retained, and the membrane plant has a first outlet for removal of retentate mixture containing the retained catalyst and a second outlet for removal of permeate mixture.

* * * * *